(12) United States Patent
Porges et al.

(10) Patent No.: US 8,133,176 B2
(45) Date of Patent: *Mar. 13, 2012

(54) METHOD AND CIRCUIT FOR INDICATING QUALITY AND ACCURACY OF PHYSIOLOGICAL MEASUREMENTS

(75) Inventors: Charles Porges, Orinda, CA (US); Clark Baker, Castro Valley, CA (US); Thomas J. Yorkey, San Ramon, CA (US); Michael Bernstein, San Ramon, CA (US); Paul Mannheimer, Danville, CA (US)

(73) Assignee: Tyco Healthcare Group LP, Mansfield, MA (US)

( * ) Notice: Subject to any disclaimer, the term of this patent is extended or adjusted under 35 U.S.C. 154(b) by 1910 days.

This patent is subject to a terminal disclaimer.

(21) Appl. No.: 11/241,635

(22) Filed: Sep. 30, 2005

(65) Prior Publication Data

US 2006/0030764 A1 Feb. 9, 2006

Related U.S. Application Data

(63) Continuation of application No. 10/712,895, filed on Nov. 12, 2003, now Pat. No. 7,457,652, which is a continuation of application No. 09/545,170, filed on Apr. 6, 2000, now Pat. No. 6,675,031.

(60) Provisional application No. 60/129,170, filed on Apr. 14, 1999.

(51) Int. Cl.
*A61B 5/00* (2006.01)
*A61B 5/1455* (2006.01)

(52) U.S. Cl. .................. 600/300; 600/323; 600/330

(58) Field of Classification Search .......... 600/309–344, 600/356
See application file for complete search history.

(56) References Cited

U.S. PATENT DOCUMENTS

| 3,638,640 A | 2/1972 | Shaw |
| 3,721,813 A | 3/1973 | Condon et al. |

(Continued)

FOREIGN PATENT DOCUMENTS

DE 69123448 5/1997

(Continued)

OTHER PUBLICATIONS

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

(Continued)

*Primary Examiner* — Eric Winakur
*Assistant Examiner* — Chu Chuan (J J) Liu
(74) *Attorney, Agent, or Firm* — Fletcher Yoder

(57) ABSTRACT

Sensors and monitors for a physiological monitoring system having capability to indicate an accuracy of an estimated physiological condition. The sensor senses at least one physiological characteristic of a patient and is connectable to a monitor that estimates the physiological condition from signals detected by the sensor. The sensor includes a detector for detecting the signals from the patient which are indicative of the physiological characteristic. The sensor is associated with a memory configured to store data that defines at least one sensor signal specification boundary for the detected signals. The boundary is indicative of a quality of the signals and an accuracy of the physiological characteristic estimated from the signals by the monitor. The sensor further includes means for providing access to the memory to allow transmission of the data that defines the at least one sensor boundary to the monitor.

41 Claims, 11 Drawing Sheets

U.S. PATENT DOCUMENTS

| | | |
|---|---|---|
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,858,615 A | 8/1989 | Meinema |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,972,331 A | 11/1990 | Chance |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,119,815 A | 6/1992 | Chance |
| 5,122,974 A | 6/1992 | Chance |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |

| | | |
|---|---|---|
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,830,139 A | 11/1998 | Abreu |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |

| | | | | | | |
|---|---|---|---|---|---|---|
| 5,846,190 | A | 12/1998 | Woehrle | 6,083,172 A | 7/2000 | Baker, Jr. et al. |
| 5,851,178 | A | 12/1998 | Aronow | 6,088,607 A | 7/2000 | Diab et al. |
| 5,851,179 | A | 12/1998 | Ritson et al. | 6,094,592 A | 7/2000 | Yorkey et al. |
| 5,853,364 | A | 12/1998 | Baker, Jr. et al. | 6,095,974 A | 8/2000 | Shemwell et al. |
| 5,860,919 | A | 1/1999 | Kiani-Azarbayjany et al. | 6,104,938 A | 8/2000 | Huiku et al. |
| 5,865,736 | A | 2/1999 | Baker, Jr. et al. | 6,112,107 A | 8/2000 | Hannula |
| 5,871,442 | A | 2/1999 | Madarasz et al. | 6,113,541 A | 9/2000 | Dias et al. |
| 5,873,821 | A | 2/1999 | Chance et al. | 6,115,621 A | 9/2000 | Chin |
| 5,879,294 | A | 3/1999 | Anderson et al. | 6,120,460 A | 9/2000 | Abreu |
| 5,885,213 | A | 3/1999 | Richardson et al. | 6,122,535 A | 9/2000 | Kaestle et al. |
| 5,890,929 | A | 4/1999 | Mills et al. | 6,133,994 A | 10/2000 | Mathews et al. |
| 5,891,021 | A | 4/1999 | Dillon et al. | 6,134,460 A | 10/2000 | Chance |
| 5,891,022 | A | 4/1999 | Pologe | 6,135,952 A | 10/2000 | Coetzee |
| 5,891,024 | A | 4/1999 | Jarman et al. | 6,144,444 A | 11/2000 | Haworth et al. |
| 5,891,025 | A | 4/1999 | Buschmann et al. | 6,144,867 A | 11/2000 | Walker et al. |
| 5,891,026 | A | 4/1999 | Wang et al. | 6,144,868 A | 11/2000 | Parker |
| 5,902,235 | A | 5/1999 | Lewis et al. | 6,149,481 A | 11/2000 | Wang et al. |
| 5,910,108 | A | 6/1999 | Solenberger | 6,150,951 A | 11/2000 | Olejniczak |
| 5,911,690 | A | 6/1999 | Rall | 6,151,107 A | 11/2000 | Schöllermann et al. |
| 5,912,656 | A | 6/1999 | Tham et al. | 6,151,518 A | 11/2000 | Hayashi |
| 5,913,819 | A | 6/1999 | Taylor et al. | 6,152,754 A | 11/2000 | Gerhardt et al. |
| 5,916,154 | A | 6/1999 | Hobbs et al. | 6,154,667 A | 11/2000 | Miura et al. |
| 5,916,155 | A | 6/1999 | Levinson et al. | 6,157,850 A | 12/2000 | Diab et al. |
| 5,919,133 | A | 7/1999 | Taylor et al. | 6,163,715 A | 12/2000 | Larsen et al. |
| 5,919,134 | A | 7/1999 | Diab | 6,165,005 A | 12/2000 | Mills et al. |
| 5,920,263 | A | 7/1999 | Huttenhoff et al. | 6,173,196 B1 | 1/2001 | Delonzor et al. |
| 5,921,921 | A | 7/1999 | Potratz et al. | 6,178,343 B1 | 1/2001 | Bindszus et al. |
| 5,922,607 | A | 7/1999 | Bernreuter | 6,181,958 B1 | 1/2001 | Steuer et al. |
| 5,924,979 | A | 7/1999 | Swedlow et al. | 6,181,959 B1 | 1/2001 | Schöllermann et al. |
| 5,924,980 | A | 7/1999 | Coetzee | 6,184,521 B1 | 2/2001 | Coffin, IV et al. |
| 5,924,982 | A | 7/1999 | Chin | 6,188,470 B1 | 2/2001 | Grace |
| 5,924,985 | A | 7/1999 | Jones | 6,192,260 B1 | 2/2001 | Chance |
| 5,934,277 | A | 8/1999 | Mortz | 6,195,575 B1 | 2/2001 | Levinson |
| 5,934,925 | A | 8/1999 | Tobler et al. | 6,198,951 B1 | 3/2001 | Kosuda et al. |
| 5,940,182 | A | 8/1999 | Lepper, Jr. et al. | 6,206,830 B1 | 3/2001 | Diab et al. |
| 5,954,644 | A | 9/1999 | Dettling et al. | 6,213,952 B1 | 4/2001 | Finarov et al. |
| 5,960,610 | A | 10/1999 | Levinson et al. | 6,217,523 B1 | 4/2001 | Amano et al. |
| 5,961,450 | A | 10/1999 | Merchant et al. | 6,222,189 B1 | 4/2001 | Misner et al. |
| 5,961,452 | A | 10/1999 | Chung et al. | 6,226,539 B1 | 5/2001 | Potratz |
| 5,964,701 | A | 10/1999 | Asada et al. | 6,226,540 B1 | 5/2001 | Bernreuter et al. |
| 5,971,930 | A | 10/1999 | Elghazzawi | 6,229,856 B1 | 5/2001 | Diab et al. |
| 5,978,691 | A | 11/1999 | Mills | 6,230,035 B1 | 5/2001 | Aoyagi et al. |
| 5,978,693 | A | 11/1999 | Hamilton et al. | 6,233,470 B1 | 5/2001 | Tsuchiya |
| 5,983,122 | A | 11/1999 | Jarman et al. | 6,236,871 B1 | 5/2001 | Tsuchiya |
| 5,987,343 | A | 11/1999 | Kinast | 6,236,872 B1 | 5/2001 | Diab et al. |
| 5,991,648 | A | 11/1999 | Levin | 6,240,305 B1 | 5/2001 | Tsuchiya |
| 5,995,855 | A | 11/1999 | Kiani et al. | 6,253,097 B1 | 6/2001 | Aronow et al. |
| 5,995,856 | A | 11/1999 | Mannheimer et al. | 6,253,098 B1 | 6/2001 | Walker et al. |
| 5,995,858 | A | 11/1999 | Kinast | 6,256,523 B1 | 7/2001 | Diab et al. |
| 5,995,859 | A | 11/1999 | Takahashi | 6,256,524 B1 | 7/2001 | Walker et al. |
| 5,997,343 | A | 12/1999 | Mills et al. | 6,261,236 B1 | 7/2001 | Grimblatov |
| 5,999,834 | A | 12/1999 | Wang et al. | 6,263,221 B1 | 7/2001 | Chance et al. |
| 6,002,952 | A | 12/1999 | Diab et al. | 6,263,222 B1 | 7/2001 | Diab et al. |
| 6,005,658 | A | 12/1999 | Kaluza et al. | 6,263,223 B1 | 7/2001 | Shepherd et al. |
| 6,006,120 | A | 12/1999 | Levin | 6,266,546 B1 | 7/2001 | Steuer et al. |
| 6,011,985 | A | 1/2000 | Athan et al. | 6,266,547 B1 | 7/2001 | Walker et al. |
| 6,011,986 | A | 1/2000 | Diab et al. | 6,272,363 B1 | 8/2001 | Casciani et al. |
| 6,014,576 | A | 1/2000 | Raley et al. | 6,278,522 B1 | 8/2001 | Lepper, Jr. et al. |
| 6,018,673 | A | 1/2000 | Chin et al. | 6,280,213 B1 | 8/2001 | Tobler et al. |
| 6,018,674 | A | 1/2000 | Aronow | 6,280,381 B1 | 8/2001 | Malin et al. |
| 6,022,321 | A | 2/2000 | Amano et al. | 6,285,894 B1 | 9/2001 | Oppelt et al. |
| 6,023,541 | A | 2/2000 | Merchant et al. | 6,285,895 B1 | 9/2001 | Ristolainen et al. |
| 6,026,312 | A | 2/2000 | Shemwell et al. | 6,285,896 B1 | 9/2001 | Tobler et al. |
| 6,026,314 | A | 2/2000 | Amerov et al. | 6,298,252 B1 | 10/2001 | Kovach et al. |
| 6,031,603 | A | 2/2000 | Fine et al. | 6,308,089 B1 | 10/2001 | Von der Ruhr et al. |
| 6,035,223 | A | 3/2000 | Baker, Jr. | 6,312,393 B1 | 11/2001 | Abreu |
| 6,036,642 | A | 3/2000 | Diab et al. | 6,321,100 B1 | 11/2001 | Parker |
| 6,041,247 | A | 3/2000 | Weckstrom et al. | 6,330,468 B1 | 12/2001 | Scharf |
| 6,044,283 | A | 3/2000 | Fein et al. | 6,334,065 B1 | 12/2001 | Al-Ali et al. |
| 6,047,201 | A | 4/2000 | Jackson, III | 6,339,715 B1 | 1/2002 | Bahr et al. |
| 6,061,584 | A | 5/2000 | Lovejoy et al. | 6,343,223 B1 | 1/2002 | Chin et al. |
| 6,064,898 | A | 5/2000 | Aldrich | 6,343,224 B1 | 1/2002 | Parker |
| 6,064,899 | A | 5/2000 | Fein et al. | 6,349,228 B1 | 2/2002 | Kiani et al. |
| 6,067,462 | A | 5/2000 | Diab et al. | 6,351,658 B1 | 2/2002 | Middleman et al. |
| 6,073,038 | A | 6/2000 | Wang et al. | 6,353,750 B1 | 3/2002 | Kimura et al. |
| 6,078,833 | A | 6/2000 | Hueber | 6,356,774 B1 | 3/2002 | Bernstein et al. |
| 6,081,735 | A | 6/2000 | Diab et al. | 6,360,113 B1 | 3/2002 | Dettling |
| 6,081,742 | A | 6/2000 | Amano et al. | 6,360,114 B1 | 3/2002 | Diab et al. |
| 6,083,157 | A | 7/2000 | Noller | 6,361,501 B1 | 3/2002 | Amano et al. |

| | | | | | | |
|---|---|---|---|---|---|---|
| 6,363,269 | B1 | 3/2002 | Hanna et al. | 6,591,122 B2 | 7/2003 | Schmitt |
| 6,370,408 | B1 | 4/2002 | Merchant et al. | 6,591,123 B2 | 7/2003 | Fein et al. |
| 6,370,409 | B1 | 4/2002 | Chung et al. | 6,594,511 B2 | 7/2003 | Stone et al. |
| 6,374,129 | B1 | 4/2002 | Chin et al. | 6,594,512 B2 | 7/2003 | Huang |
| 6,377,829 | B1 | 4/2002 | Al-Ali et al. | 6,594,513 B1 | 7/2003 | Jobsis et al. |
| 6,381,479 | B1 | 4/2002 | Norris | 6,597,931 B1 | 7/2003 | Cheng et al. |
| 6,381,480 | B1 | 4/2002 | Stoddar et al. | 6,597,933 B2 | 7/2003 | Kiani et al. |
| 6,385,471 | B1 | 5/2002 | Mortz | 6,600,940 B1 | 7/2003 | Fein et al. |
| 6,385,821 | B1 | 5/2002 | Modgil et al. | 6,606,509 B2 | 8/2003 | Schmitt |
| 6,388,240 | B2 | 5/2002 | Schulz et al. | 6,606,510 B2 | 8/2003 | Swedlow et al. |
| 6,393,310 | B1 | 5/2002 | Kuenster | 6,606,511 B1 | 8/2003 | Ali et al. |
| 6,397,091 | B2 | 5/2002 | Diab et al. | 6,606,512 B2 | 8/2003 | Muz et al. |
| 6,397,092 | B1 | 5/2002 | Norris et al. | 6,615,064 B1 | 9/2003 | Aldrich |
| 6,397,093 | B1 | 5/2002 | Aldrich | 6,615,065 B1 | 9/2003 | Barrett et al. |
| 6,400,971 | B1 | 6/2002 | Finarov et al. | 6,618,602 B2 | 9/2003 | Levin et al. |
| 6,400,972 | B1 | 6/2002 | Fine | 6,622,034 B1 | 9/2003 | Gorski et al. |
| 6,402,690 | B1 | 6/2002 | Rhee et al. | 6,622,095 B2 | 9/2003 | Kobayashi et al. |
| 6,408,198 | B1 | 6/2002 | Hanna et al. | 6,628,975 B1 | 9/2003 | Fein et al. |
| 6,411,832 | B1 | 6/2002 | Guthermann | 6,631,281 B1 | 10/2003 | Kästle |
| 6,411,833 | B1 | 6/2002 | Baker, Jr. et al. | 6,643,530 B2 | 11/2003 | Diab et al. |
| 6,415,236 | B2 | 7/2002 | Kobayashi et al. | 6,643,531 B1 | 11/2003 | Katarow |
| 6,419,671 | B1 | 7/2002 | Lemberg | 6,647,279 B2 | 11/2003 | Pologe |
| 6,421,549 | B1 | 7/2002 | Jacques | 6,647,280 B2 | 11/2003 | Bahr et al. |
| 6,430,423 | B2 | 8/2002 | DeLonzor et al. | 6,650,917 B2 | 11/2003 | Diab et al. |
| 6,430,513 | B1 | 8/2002 | Wang et al. | 6,650,918 B2 | 11/2003 | Terry |
| 6,430,525 | B1 | 8/2002 | Weber et al. | 6,654,621 B2 | 11/2003 | Palatnik et al. |
| 6,434,408 | B1 | 8/2002 | Heckel et al. | 6,654,622 B1 | 11/2003 | Eberhard et al. |
| 6,438,399 | B1 | 8/2002 | Kurth | 6,654,623 B1 | 11/2003 | Kästle |
| 6,449,501 | B1 | 9/2002 | Reuss | 6,654,624 B2 | 11/2003 | Diab et al. |
| 6,453,183 | B1 | 9/2002 | Walker | 6,658,276 B2 | 12/2003 | Kianl et al. |
| 6,453,184 | B1 | 9/2002 | Hyogo et al. | 6,658,277 B2 | 12/2003 | Wasserman |
| 6,456,862 | B2 | 9/2002 | Benni | 6,662,030 B2 | 12/2003 | Khalil et al. |
| 6,461,305 | B1 | 10/2002 | Schnall | 6,662,033 B2 | 12/2003 | Casciani et al. |
| 6,463,310 | B1 | 10/2002 | Swedlow et al. | 6,665,551 B1 | 12/2003 | Suzuki |
| 6,463,311 | B1 | 10/2002 | Diab | 6,668,182 B2 | 12/2003 | Hubelbank |
| 6,466,808 | B1 | 10/2002 | Chin et al. | 6,668,183 B2 | 12/2003 | Hicks et al. |
| 6,466,809 | B1 | 10/2002 | Riley | 6,671,526 B1 | 12/2003 | Aoyagi et al. |
| 6,470,199 | B1 | 10/2002 | Kopotic et al. | 6,671,528 B2 | 12/2003 | Steuer et al. |
| 6,470,200 | B2 | 10/2002 | Walker et al. | 6,671,530 B2 | 12/2003 | Chung et al. |
| 6,480,729 | B2 | 11/2002 | Stone | 6,671,531 B2 | 12/2003 | Al-Ali et al. |
| 6,487,439 | B1 | 11/2002 | Skladnev et al. | 6,671,532 B1 | 12/2003 | Fudge et al. |
| 6,490,466 | B1 | 12/2002 | Fein et al. | 6,675,031 B1 | 1/2004 | Porges et al. |
| 6,496,711 | B1 | 12/2002 | Athan et al. | 6,678,543 B2 | 1/2004 | Diab et al. |
| 6,498,942 | B1 | 12/2002 | Esenaliev et al. | 6,681,126 B2 | 1/2004 | Solenberger |
| 6,501,974 | B2 | 12/2002 | Huiku | 6,681,128 B2 | 1/2004 | Steuer et al. |
| 6,501,975 | B2 | 12/2002 | Diab et al. | 6,681,454 B2 | 1/2004 | Modgil et al. |
| 6,505,060 | B1 | 1/2003 | Norris | 6,684,090 B2 | 1/2004 | Ali et al. |
| 6,505,061 | B2 | 1/2003 | Larson | 6,684,091 B2 | 1/2004 | Parker |
| 6,505,133 | B1 | 1/2003 | Hanna et al. | 6,690,958 B1 | 2/2004 | Walker et al. |
| 6,510,329 | B2 | 1/2003 | Heckel | 6,694,160 B2 | 2/2004 | Chin |
| 6,510,331 | B1 | 1/2003 | Williams et al. | 6,697,653 B2 | 2/2004 | Hanna |
| 6,512,937 | B2 | 1/2003 | Blank et al. | 6,697,655 B2 | 2/2004 | Sueppel et al. |
| 6,515,273 | B2 | 2/2003 | Al-Ali | 6,697,656 B1 | 2/2004 | Al-Ali |
| 6,519,484 | B1 | 2/2003 | Lovejoy et al. | 6,697,658 B2 | 2/2004 | Al-Ali |
| 6,519,486 | B1 | 2/2003 | Edgar, Jr. et al. | RE38,476 E | 3/2004 | Diab et al. |
| 6,519,487 | B1 | 2/2003 | Parker | 6,699,194 B1 | 3/2004 | Diab et al. |
| 6,525,386 | B1 | 2/2003 | Mills et al. | 6,699,199 B2 | 3/2004 | Asada et al. |
| 6,526,300 | B1 | 2/2003 | Kiani et al. | 6,701,170 B2 | 3/2004 | Stetson |
| 6,526,301 | B2 | 2/2003 | Larsen et al. | 6,702,752 B2 | 3/2004 | Dekker |
| 6,541,756 | B2 | 4/2003 | Schulz et al. | 6,707,257 B2 | 3/2004 | Norris |
| 6,542,764 | B1 | 4/2003 | Al-Ali et al. | 6,708,048 B1 | 3/2004 | Chance |
| 6,544,193 | B2 | 4/2003 | Abreu | 6,708,049 B1 | 3/2004 | Berson et al. |
| 6,546,267 | B1 | 4/2003 | Sugiura et al. | 6,709,402 B2 | 3/2004 | Dekker |
| 6,549,795 | B1 | 4/2003 | Chance | 6,711,424 B1 | 3/2004 | Fine et al. |
| 6,553,241 | B2 | 4/2003 | Mannheimer et al. | 6,711,425 B1 | 3/2004 | Reuss |
| 6,553,242 | B1 | 4/2003 | Sarussi | 6,714,803 B1 | 3/2004 | Mortz |
| 6,553,243 | B2 | 4/2003 | Gurley | 6,714,804 B2 | 3/2004 | Al-Ali et al. |
| 6,556,852 | B1 | 4/2003 | Schulze et al. | 6,714,805 B2 | 3/2004 | Jeon et al. |
| 6,560,470 | B1 | 5/2003 | Pologe | RE38,492 E | 4/2004 | Diab et al. |
| 6,564,077 | B2 | 5/2003 | Mortara | 6,719,686 B2 | 4/2004 | Coakley et al. |
| 6,564,088 | B1 | 5/2003 | Soller et al. | 6,719,705 B2 | 4/2004 | Mills |
| 6,571,113 | B1 | 5/2003 | Fein et al. | 6,720,734 B2 | 4/2004 | Norris |
| 6,571,114 | B1 | 5/2003 | Koike et al. | 6,721,584 B2 | 4/2004 | Baker, Jr. et al. |
| 6,574,491 | B2 | 6/2003 | Elghazzawi | 6,721,585 B1 | 4/2004 | Parker |
| 6,580,086 | B1 | 6/2003 | Schulz et al. | 6,725,074 B1 | 4/2004 | Kästle |
| 6,584,336 | B1 | 6/2003 | Ali et al. | 6,725,075 B2 | 4/2004 | Al-Ali |
| 6,587,703 | B2 | 7/2003 | Cheng et al. | 6,731,963 B2 | 5/2004 | Finarov et al. |
| 6,587,704 | B1 | 7/2003 | Fine et al. | 6,731,967 B1 | 5/2004 | Turcott |
| 6,589,172 | B2 | 7/2003 | Williams et al. | 6,735,459 B2 | 5/2004 | Parker |

| | | |
|---|---|---|
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,785,568 B2 | 8/2004 | Chance |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,949,081 B1 | 9/2005 | Chance |
| 6,950,687 B2 | 9/2005 | Al-Ali |
| 6,961,598 B2 | 11/2005 | Diab |
| 6,963,767 B2 | 11/2005 | Rantala et al. |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,048,687 B1 | 5/2006 | Reuss et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,054 B2 | 8/2006 | Adbul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Achilefu et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,236,881 B2 | 6/2007 | Liu et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Scmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,428,432 B2 | 9/2008 | Ali et al. |
| 7,457,652 B2 | 11/2008 | Porges et al. |
| 2001/0005773 A1 | 6/2001 | Larsen et al. |
| 2001/0020122 A1 | 9/2001 | Steuer et al. |
| 2001/0021803 A1 | 9/2001 | Blank et al. |
| 2001/0039376 A1 | 11/2001 | Steuer et al. |
| 2001/0044700 A1 | 11/2001 | Kobayashi et al. |
| 2001/0051767 A1 | 12/2001 | Williams et al. |
| 2002/0026106 A1 | 2/2002 | Khalil et al. |
| 2002/0026109 A1 | 2/2002 | Diab et al. |
| 2002/0028990 A1 | 3/2002 | Shepherd et al. |
| 2002/0035318 A1 | 3/2002 | Mannheimer et al. |
| 2002/0038078 A1 | 3/2002 | Ito |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0068859 A1 | 6/2002 | Knopp |
| 2002/0111748 A1 | 8/2002 | Kobayashi et al. |
| 2002/0128544 A1 | 9/2002 | Diab et al. |
| 2002/0133067 A1 | 9/2002 | Jackson, III |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2002/0198443 A1 | 12/2002 | Ting |
| 2003/0018243 A1 | 1/2003 | Gerhardt et al. |

| | | |
|---|---|---|
| 2003/0023140 A1 | 1/2003 | Chance |
| 2003/0036690 A1 | 2/2003 | Geddes et al. |
| 2003/0045785 A1 | 3/2003 | Diab et al. |
| 2003/0055324 A1 | 3/2003 | Wasserman |
| 2003/0060693 A1 | 3/2003 | Monfre et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0139687 A1 | 7/2003 | Abreu |
| 2003/0144584 A1 | 7/2003 | Mendelson |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0220548 A1 | 11/2003 | Schmitt |
| 2003/0220576 A1 | 11/2003 | Diab |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054270 A1 | 3/2004 | Pewzner et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0127779 A1 | 7/2004 | Steuer et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176670 A1 | 9/2004 | Takamura et al. |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230106 A1 | 11/2004 | Schmitt et al. |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0065417 A1 | 3/2005 | Ali et al. |
| 2005/0075550 A1 | 4/2005 | Lindekugel |
| 2005/0080323 A1 | 4/2005 | Kato |
| 2005/0101850 A1 | 5/2005 | Parker |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0197548 A1 | 9/2005 | Dietiker |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0277819 A1 | 12/2005 | Kiani et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0025660 A1 | 2/2006 | Swedlow et al. |
| 2006/0030763 A1 | 2/2006 | Mannheimer et al. |
| 2006/0030764 A1 | 2/2006 | Porges et al. |
| 2006/0052680 A1 | 3/2006 | Diab |
| 2006/0058594 A1 | 3/2006 | Ishizuka et al. |
| 2006/0058683 A1 | 3/2006 | Chance |
| 2006/0064024 A1 | 3/2006 | Schnall |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0161054 A1 | 7/2006 | Reuss et al. |
| 2006/0195028 A1 | 8/2006 | Hannula et al. |
| 2006/0224058 A1 | 10/2006 | Mannheimer |
| 2006/0224059 A1 | 10/2006 | Swedlow et al. |
| 2006/0247501 A1 | 11/2006 | Ali |
| 2006/0258921 A1 | 11/2006 | Addison et al. |
| 2006/0258926 A1 | 11/2006 | Ali et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073126 A1 | 3/2007 | Raridan, Jr. |
| 2007/0112260 A1 | 5/2007 | Diab et al. |
| 2008/0039701 A1 | 2/2008 | Ali et al. |

FOREIGN PATENT DOCUMENTS

| | | |
|---|---|---|
| EP | 0 221 357 A1 | 5/1987 |
| EP | 0352923 | 1/1990 |
| EP | 0 571 225 A1 | 11/1993 |
| EP | 0 571 225 A3 | 11/1993 |
| EP | 0630203 | 12/1994 |
| EP | 1491135 | 12/2004 |
| JP | 3170866 | 7/1991 |
| JP | 3238813 | 10/1991 |
| JP | 4332536 | 11/1992 |
| JP | 6154177 | 6/1994 |
| JP | 7124138 | 5/1995 |
| JP | 7136150 | 5/1995 |
| JP | 2003194714 | 7/2003 |
| JP | 2003210438 | 7/2003 |
| JP | 2004008572 | 1/2004 |
| JP | 2004113353 | 4/2004 |

| | | |
|---|---|---|
| JP | 2004194908 | 7/2004 |
| JP | 2004248819 | 9/2004 |
| JP | 2004290545 | 10/2004 |
| WO | WO9101678 | 2/1991 |
| WO | WO9309711 | 5/1993 |
| WO | WO9423643 | 10/1994 |
| WO | WO95/16387 | 6/1995 |
| WO | WO9843071 | 10/1998 |
| WO | WO9932030 | 7/1999 |
| WO | WO0021438 | 4/2000 |
| WO | WO 00/61000 A1 | 10/2000 |
| WO | WO0059374 | 10/2000 |
| WO | WO03011127 | 2/2003 |

OTHER PUBLICATIONS

Barreto, Armando B., et al.; "Adaptive LMS Delay Measurement in dual Blood Volume Pulse Signals for Non-Invasive Monitoring," *IEEE*, pp. 117-120 (1997).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Cysewska-Sobusiak, Anna; "Metrological Problems With noninvasive Transillumination of Living Tissues," *Proceedings of SPIE*, vol. 4515, pp. 15-24 (2001).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Goldman, Julian M.; "Masimo Signal Extraction Pulse Oximetry," *Journal of Clinical Monitoring and Computing*, vol. 16, pp. 475-483 (2000).

Hamilton, Patrick S., et al.; "Effect of Adaptive Motion-Artifact Reduction on QRS Detection," *Biomedical Instrumentation & Technology*, pp. 197-202 (undated).

J. Huang, et al.; "Low Power Motion Tolerant Pulse Oximetry," *Abstracts*, A7, p. S103. (undated).

Johansson, A., "Neural network for photoplethysmographic respiratory rate monitoring," *Medical & Biological Engineering & Computing*, vol. 41, pp. 242-248 (2003).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform," pp. II-310-II-311 (undated).

Leahy, Martin J., et al.; "Sensor Validation in Biomedical Applications," *IFAC Modelling and Control in Biomedical Systems*, Warwick, UK; pp. 221-226 (1997).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Maletras, Francois-Xavier, et al.; "Construction and calibration of a new design of Fiber Optic Respiratory Plethysmograph (FORP)," Optomechanical Design and Engineering, *Proceedings of SPIE*, vol. 4444, pp. 285-293 (2001).

Odagiri, Y.; "Pulse Wave Measuring Device," *Micromechatronics*, vol. 42, No. 3, pp. 6-11 (undated) (Article in Japanese—contains English summary of article).

R. Neumann, et al.; "Fourier Artifact suppression Technology Provides Reliable $SpO_2$," *Abstracts*, A11, p. S105. (undated).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," Dissertation, (1998).

Todd, Bryan, et al.; "The Identification of Peaks in Physiological Signals," *Computers and Biomedical Research*, vol. 32, pp. 322-335 (1999).

METHOD AND CIRCUIT FOR INDICATING QUALITY AND ACCURACY OF PHYSIOLOGICAL MEASUREMENTS

CROSS-REFERENCE TO RELATED APPLICATIONS

This application is a Continuation of U.S. application Ser. No. 10/712,895, filed Nov. 12, 2003 now U.S. Pat. No. 7,457, 652, which is a continuation of U.S. application Ser. No. 09/545,170, filed Apr. 6, 2000, now U.S. Pat. No. 6,675,031, which claims the benefit of U.S. Provisional Application No. 60/129,170, filed on Apr. 14, 1999, the disclosures of which are hereby incorporated.

BACKGROUND OF THE INVENTION

The present invention relates to physiological monitoring instruments and, in particular, monitors and sensors that include mechanisms for indicating a quality of detected signals and accuracy or confidence level of physiological measurements estimated from the signals.

Typically, for physiological monitoring instruments that include a monitor and a patient sensor, the monitor is unable to accurately determine a quality of a signal obtained from the sensor. The invention will be explained by reference to a preferred embodiment concerning pulse oximeter monitors and pulse oximetry sensors, but it should be realized the invention is applicable to any generalized patient monitor and associated patient sensor. The invention provides a way of more accurately determining a quality of a signal detected by a sensor; a way of determining a relative accuracy of a physiological characteristic derived or calculated from the signal; and a way of delineating a transition boundary between a normal signal for the sensor being used in its normal application, and a signal considered to be abnormal for the sensor being used, to allow a monitor to determine if the sensor is being misapplied.

Pulse oximetry is typically used to measure various blood flow characteristics including, but not limited to, the blood oxygen saturation of hemoglobin in arterial blood and the heartbeat of a patient. Measurement of these characteristics has been accomplished by the use of a non-invasive sensor that passes light through a portion of a patient's blood perfused tissue and photo-electrically senses the absorption and scattering of light in such tissue. The amount of light absorbed and scattered is then used to estimate the amount of blood constituent in the tissue using various algorithms known in the art. The "pulse" in pulse oximetry comes from the time varying amount of arterial blood in the tissue during a cardiac cycle. The signal processed from the sensed optical signal is a familiar plethysmographic waveform due to the cycling light attenuation.

The light passed through the tissue is typically selected to be of two or more wavelengths that are absorbed by the blood in an amount related to the amount of blood constituent present in the blood. The amount of transmitted light that passes through the tissue varies in accordance with the changing amount of blood constituent in the tissue and the related light absorption.

To estimate arterial blood oxygen saturation of a patient, conventional two-wavelength pulse oximeters emit light from two light emitting diodes (LEDs) into a pulsatile tissue bed and collect the transmitted light with a photodiode (or photo-detector) positioned on an opposite surface (i.e., for transmission pulse oximetry) or an adjacent surface (i.e., for reflectance pulse oximetry). The LEDs and photo-detector are typically housed in a reusable or disposable oximeter sensor that couples to a pulse oximeter electronics and display unit. One of the two LEDs' primary wavelength is selected at a point in the electromagnetic spectrum where the absorption of oxyhemoglobin ($HbO_2$) differs from the absorption of reduced hemoglobin (Hb). The second of the two LEDs' wavelength is selected at a different point in the spectrum where the absorption of Hb and $HbO_2$ differs from those at the first wavelength. Commercial pulse oximeters typically utilize one wavelength in the near red part of the visible spectrum near 660 nanometers (nm) and one in the near infrared (IR) part of the spectrum in the range of 880-940 nm.

Oxygen saturation can be estimated using various techniques. In one common technique, first and second photo-current signals generated by the photo-detector from red and infrared light are conditioned and processed to determine AC and DC signal components and a modulation ratio of the red to infrared signals. This modulation ratio has been observed to correlate well to arterial oxygen saturation. Pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios. The estimation of oxygen saturation using modulation ratio is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. All three patents are assigned to the assignee of the present invention and incorporated herein by reference.

The accuracy of the estimates of the blood flow characteristics depends on a number of factors. For example, the light absorption characteristics typically vary from patient to patient depending on their physiology. Moreover, the absorption characteristics vary depending on the location (e.g., the foot, finger, ear, and so on) where the sensor is applied. Further, the light absorption characteristics vary depending on the design or model of the sensor. Also, the light absorption characteristics of any single sensor design vary from sensor to sensor (e.g., due to different characteristics of the light sources or photo-detector, or both). The clinician applying the sensor correctly or incorrectly may also have a large impact in the results, for example, by loosely or firmly applying the sensor or by applying the sensor to a body part which is inappropriate for the particular sensor design being used.

Some oximeters "qualify" measurements before displaying them on the monitor. One conventional technique processes (i.e., filters) the measured plethysmographic waveform and performs tests to detect and reject measurements perceived corrupted and inaccurate. Since oximeters are typically designed to be used with a wide variety of sensors having widely differing performance characteristics, the monitor signal "qualification" algorithms are necessarily crude, and often result in only superficial indications of signal quality, signal reliability, and ultimately a confidence level in a patient physiological characteristic estimated or calculated from the signal. In many instances, the monitor simply discards data associated with low quality signals, but otherwise gives no indication to a healthcare giver as to whether any physiological characteristic displayed on a monitor is highly reliable or not. Hence, the signal quality measurements obtained from such crude algorithms are relatively poor and convey little useful information to a caregiver.

SUMMARY OF THE INVENTION

Accordingly, it is an object of the present invention to provide a patient monitor and sensor which includes means for accurately detecting a quality of a signal detected by the sensor.

Another object of the invention is to provide a monitor and sensor which includes means for accurately determining a quality of a physical characteristic estimated from a signal obtained by a sensor.

A further object of the invention is to provide a monitor and sensor which includes means for detecting a transition between a signal regime considered normal for the sensor in its usual application, and a signal regime considered to be abnormal.

These and others objects of the invention are achieved by the use of a set of one or more signal specification boundaries. Each boundary defines a region of a signal quality diagram and corresponds to a different level of quality in the detected signals and accuracy or confidence level of physiological characteristic estimated from the detected signals. Boundaries can also be defined for and associated with different sensor types and monitor types. The boundaries are typically stored in a memory and accessed when required.

An embodiment of the invention provides a sensor for sensing at least one physiological characteristic of a patient. The sensor is connectable to a monitor that estimates a physiological condition from signals detected by the sensor. The sensor includes a detector for detecting the signals from the patient which are indicative of the physiological characteristic. The sensor is associated with a memory configured to store data that defines at least one sensor signal specification boundary for the detected signals. The boundary is indicative of a quality of the signals and an accuracy of the physiological characteristic estimated from the signals by the monitor. The sensor further includes means for providing access to the memory to allow transmission of the data that defines the at least one sensor boundary to the monitor.

In an embodiment, the boundary is indicative of a transition between a signal regime considered normal for the sensor in its usual application, and a signal regime considered to be abnormal. The normal regime can be one in which the sensor is likely to be properly applied to the patient and the abnormal regime can be one in which the sensor may have partially or entirely come off the patient.

Another embodiment of the invention provides a monitor for providing an indication of an accuracy of an estimated physiological condition of a patient. The monitor is connectable to a sensor that detects signals indicative of at least one physiological characteristic of the patient. The monitor includes at least one receiving circuit and at least one processing circuit. The receiving circuit is configured to receive the signals indicative of the at least one physiological characteristic and data defining at least one sensor signal specification boundary for the detected signals. The processing circuit is configured to estimate the physiological condition of the patient based on the received signals, compare the received signals against the at least one sensor boundary, and generate the indication of the accuracy of the estimated physiological condition. The monitor further includes means for providing the indication of the accuracy of the estimated physiological condition to a user of the monitor.

Yet another embodiment of the invention provides a pulse oximetry system that includes the sensor described above and a pulse oximetry monitor. The monitor has means to determine whether the signals are within a normal regime or an abnormal regime. The system further includes means for informing a user of the system as to whether the signal is normal or abnormal.

The foregoing, together with other aspects of this invention, will become more apparent when referring to the following specification, claims, and accompanying drawings.

DESCRIPTION OF THE SPECIFIC EMBODIMENTS

The invention is applicable to measurement (or estimation) of oxygen saturation of hemoglobin in arterial blood and patient heart rate. The invention will be described in detail with respect to an embodiment for pulse oximetry, but it needs to be realized that the invention has applicability to alternate patient monitoring characteristics, such as ECG, blood pressure, temperature, etc., and is not to be limited to only for use with oximetry or pulse oximetry.

Figure 1:
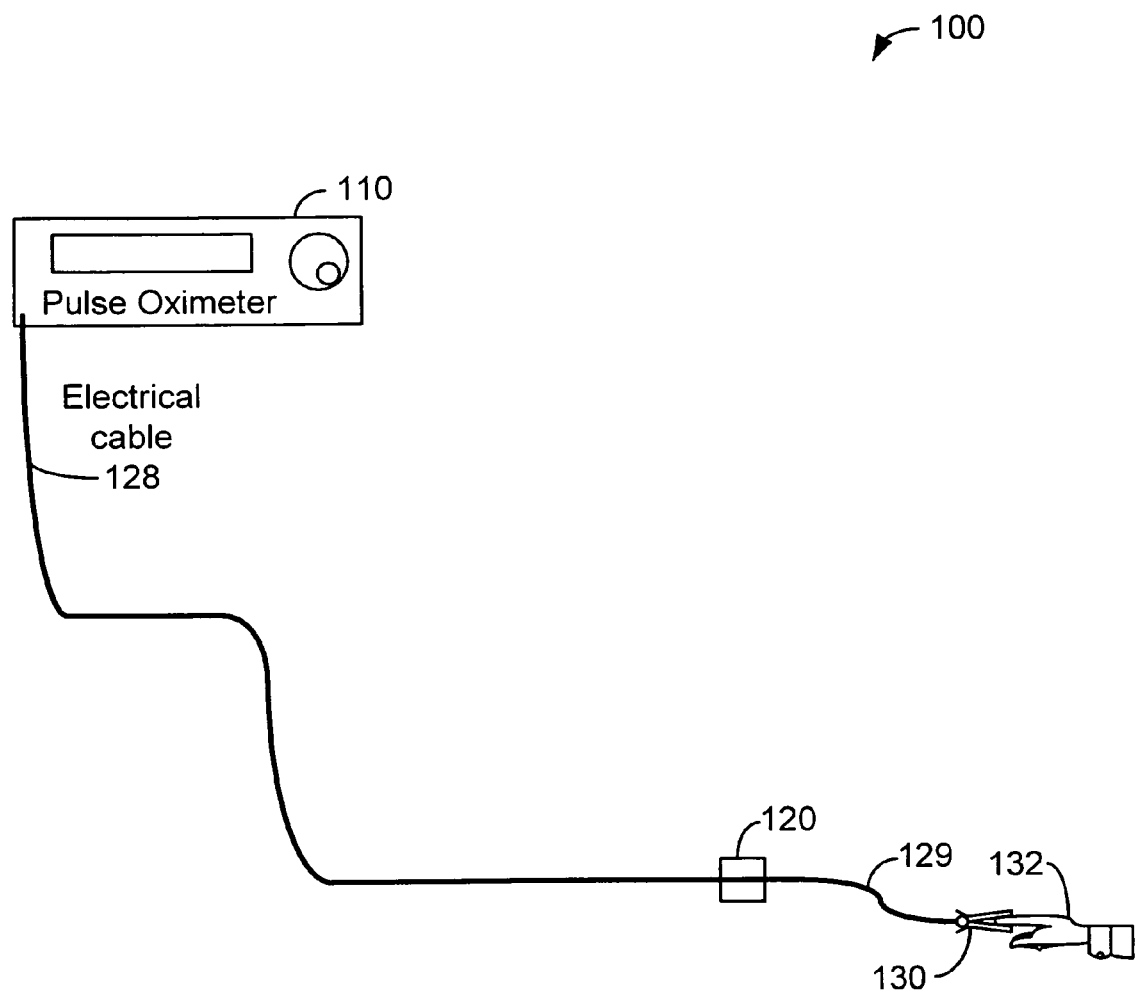
FIG. 1 shows a simplified block diagram of an embodiment of a pulse oximeter system.

FIG. 1 shows a simplified block diagram of an embodiment of a pulse oximeter system 100. System 100 includes a pulse oximeter (or monitor) 110 that couples via an electrical cable 128 to a sensor 130 that is applied to a patient 132. Sensor 130 includes a sensor cable 129 and a connector plug 120. The sensor further has first and second light sources (e.g., LEDs) and a photo-detector along with suitable components to couple these electro-optical components to the electrical cable 128.

As noted above, oxygen saturation can be estimated using various techniques. In one common technique, the optical signals are received by the photo-detector, and conditioned and processed by the oximeter to generate AC and DC components. These components are then used to compute a modulation ratio of the red to infrared signals. The computed modulation ratio is then indexed against a table to retrieve a saturation estimate corresponding to that modulation ratio.

Figure 2A:
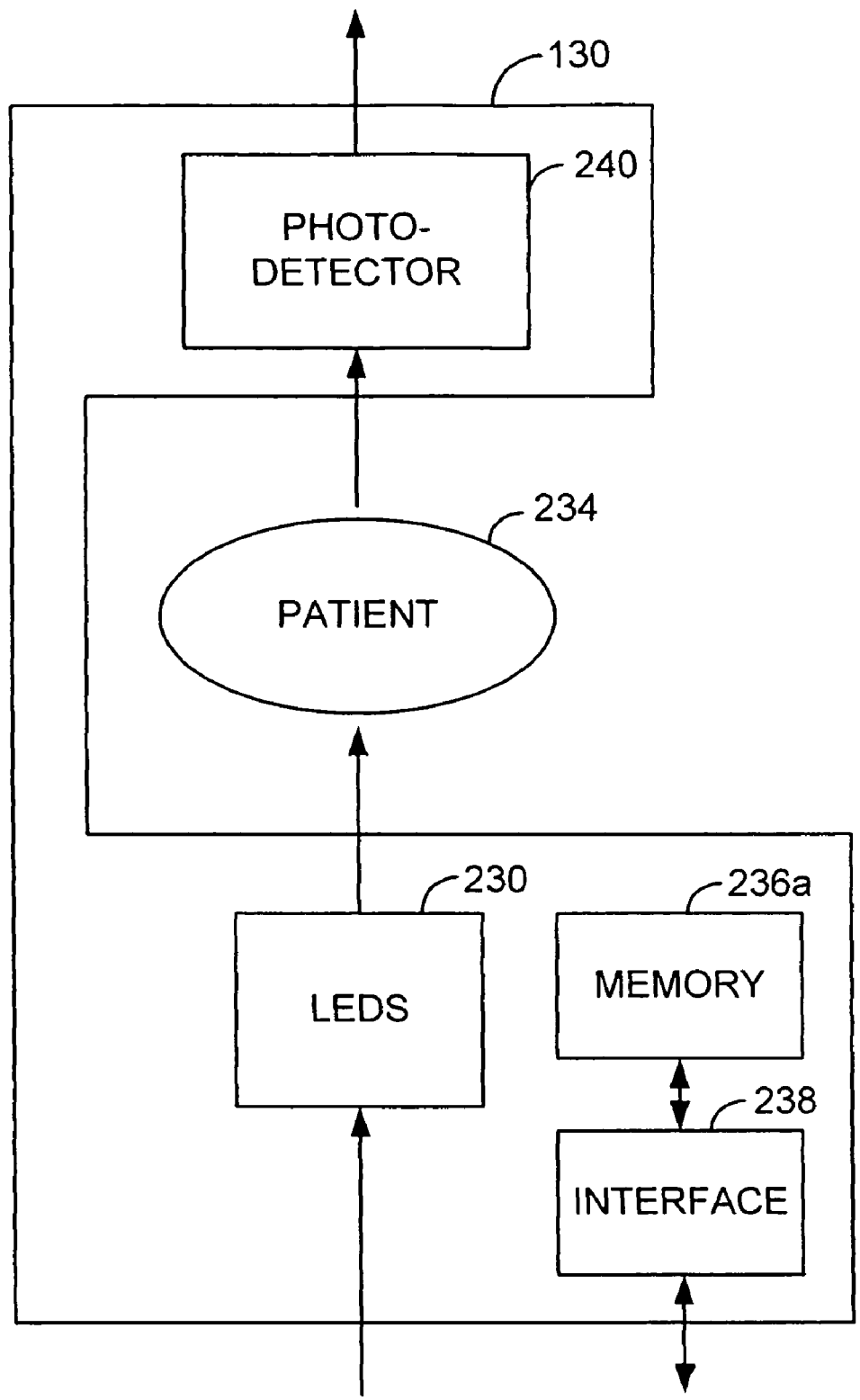
FIG. 2A shows a diagram of a specific embodiment of a sensor.

FIG. 2A shows a diagram of a specific embodiment of sensor 130. Sensor 130 includes two or more LEDs 230 and a photodetector 240. Sensor 130 may optionally include a memory 236a and an interface 238. LEDs 230 receive drive signals that (i.e., alternately) activate the LEDs. When activated, the light from LEDs 230 passes into a patient's tissues 234. After being transmitted through or reflected from the tissues, the light is received by photo-detector 240. Photo-detector 240 converts the received light into a photocurrent signal, which is then provided to the subsequent signal-processing unit.

The sensor memory stores data representative of at least one sensor signal specification boundary and provides the sensor boundary when requested. Interface circuit 238 provides signal conditioning, and can also provide other functions. Through interface circuit 238, data is transferred to and from the sensor memory. Memory 236a and interface circuit 238 can be integrated within one integrated circuit for reduced size and cost.

The memory associated with the sensor can be physically located in a variety of places. First, it can be located on the body of the sensor, in a vicinity of the photodetector, LEDs, or other sensor components. Or, the memory can be in the sensor cable 129 or the connector plug 120, or in an adapter module that connects to a front of an oximeter, to an oximeter cable, or to a sensor plug or cable.

Figure 2B:
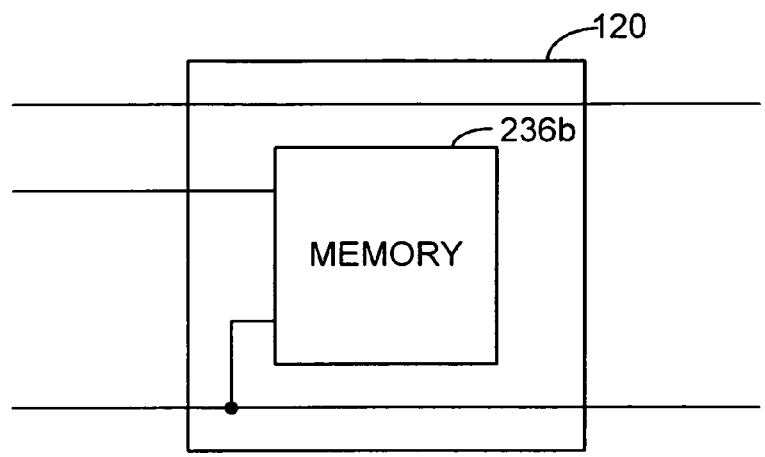
FIGS. 2B and 2C show diagrams of specific embodiments in which a memory is located within the sensor plug and within the sensor cable, respectively.

FIG. 2B shows a diagram of a specific embodiment in which a memory 236b is located within the connector plug 120. Memory 236b couples to and interfaces with external circuitry through some or all signal lines provided to the sensor plug.

Figure 2C:
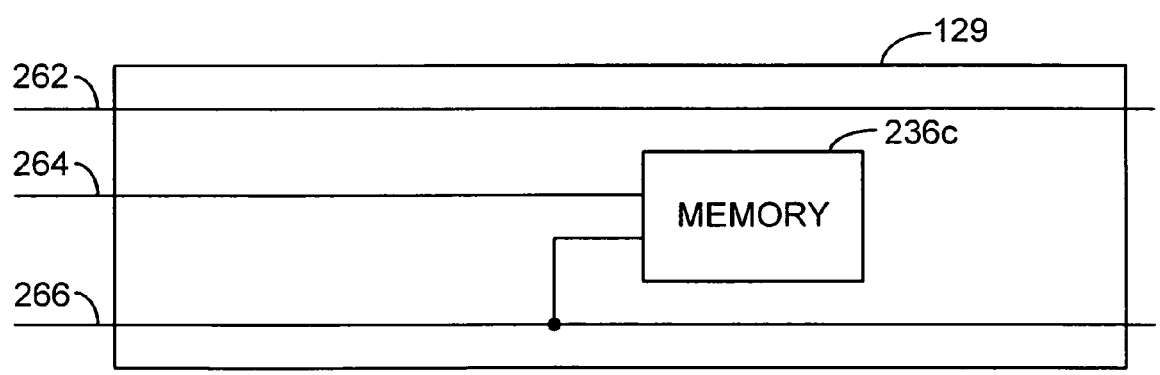

FIG. 2C shows a diagram of a specific embodiment in which a memory 236c is located within the sensor cable 129. Again, memory 236c couples to and interfaces with external circuitry through a set of signal lines.

The memory 236 can be implemented as a random access memory (RAM), a FLASH memory, a programmable read only memory (PROM), an erasable PROM (EPROM), an electrically erasable PROM (EEPROM), a write once memory, or other memory technologies capable of write and read operations. In a specific embodiment, to preserve the data stored in the memory and prevent accidental erasure, the sensor memory can be written only once. This memory characteristic also prevents erasure of the data during sensor operation. A specific example of a memory device that can be written only once is a 2-wire EPROM device available from Dallas Semiconductor Corp.

Figure 2D:
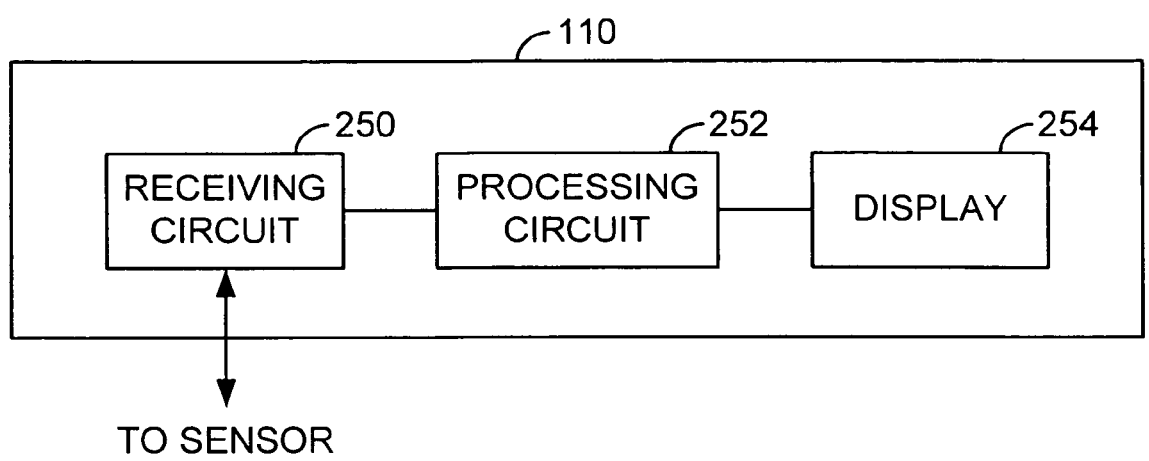
FIG. 2D shows a diagram of a specific embodiment of a monitor.

FIG. 2D shows a diagram of a specific embodiment of monitor 110. A receiving circuit 250 couples to the sensor and the memory associated with the sensor for receiving signals detected by the sensor and data from the sensor memory. The receiving circuit 250 couples to a processing circuit 252 that processes the received signals to generate an estimate of a physiological characteristic. The processing circuit 252 can further generate an indication of the quality of the received signal and an indication of the accuracy of the estimated physiological characteristic. The estimated physiological characteristic and associated indications are provided to a display unit 254 for display to a user of the monitor.

Figure 3:
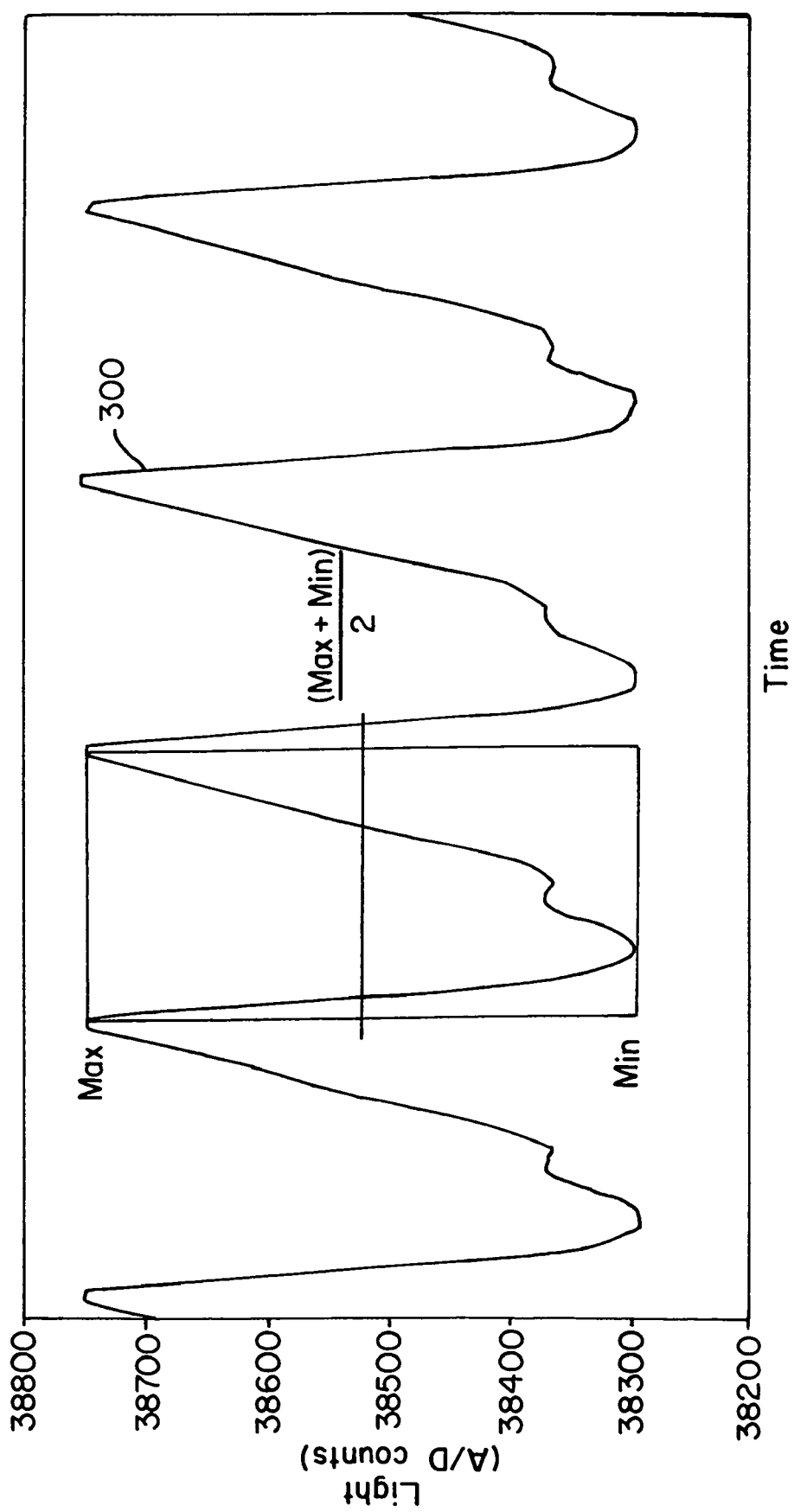
FIG. 3 shows a diagram of a simplified optical waveform detected by the sensor.

FIG. 3 shows a diagram of a simplified optical waveform 300 detected by a sensor (e.g., sensor 130). Optical waveform 300 in FIG. 3 can represent the detected optical signal for either the red or infrared LED. As shown in FIG. 3, optical waveform 300 includes a periodic pattern that generally corresponds to a patient's heartbeat. For arrhythmia patient, the waveform may be aperiodic. Waveform 300 includes a series of peaks having a maximum value (Max) and a series of valleys having a minimum value (Min). The following quantities are defined:

$$AC = \text{Max} - \text{Min};$$ Eq. (1)

$$DC = \frac{(\text{Max} - \text{Min})}{2};$$ Eq. (2)

$$\text{Modulation percentage } (Mod \, \%) = 100 \cdot \left(\frac{AC}{DC}\right); \text{ and}$$ Eq. (3)

$$nAv \text{ (nanoAmperes virtual)} = \frac{DC}{\text{Instrument gain}} \cdot \frac{50 \text{ mA}}{\text{actual } LED \text{ drive current in mA}}$$ Eq. (4)

where Instrument gain is a gain value that is specific to the combination of the pulse oximeter and a particular sensor that is used during the detection of the pulses in waveform 300. Nanoamperes virtual "normalizes" the signal to a 50 mA LED drive. Many oximeters contain servo systems which adjust LED drive intensity to be optimal for a particular set of monitoring conditions. By normalizing signal levels to a standard assumed LED drive level, it is possible to derive a measure of signal strength which is dependent primarily on the sensor and patient, and not on particular drive level which the instrument has selected.

The modulation ratio of the red to infrared signals, sometimes referred to as the "ratio of ratios" (Ratrat), can be approximated as:

$$\text{Ratrat} \cong \frac{\left(\frac{AC\_Red}{DC\_Red}\right)}{\left(\frac{AC\_IR}{DC\_IR}\right)};$$ Eq. (5)

where AC_Red and DC_Red are the respective AC and DC components of the red LED, and AC_IR and DC_IR are the respective AC and DC components of the infrared LED. Oxygenation derived from Ratrat using equation (5) is sufficiently accurate for many applications when the condition (AC<<DC) is satisfied. Particularly, the approximation error is small when both AC terms in equation (5) are less than ten percent of the related DC terms (i.e., both red and infrared modulations are less than 10%).

As stated above, oxygen saturation is related to Ratrat. The relationship between Ratrat and oxygen saturation is typically plotted as a curve (i.e., saturation versus Ratrat) and stored as a table in the memory within the oximeter. Subsequently, a calculated Ratrat is used to index the table to retrieve an entry in the table for the oxygen saturation estimate corresponding to that Ratrat. The estimation of oxygen saturation using Ratrat is further described in U.S. Pat. Nos. 4,911,167, 5,645,059, and 5,853,364.

Generally, the Red terms are measured in the red part of the optical spectrum using the red LED, and the IR terms are measured in the infrared part of the optical spectrum using the infrared LED. The AC terms are generated by the blood pressure pulse and are somewhat related to "perfusion." The DC terms are (inversely) related to the "opacity" (or darkness) of the patient being monitored and are somewhat related to "translucence." Generally, the four terms in equation (5) are independent of each other. However, empirical studies suggest that the two DC terms are somewhat correlated (i.e., not wildly divergent), and patients who are "opaque" tend to be opaque in both the red and infrared parts of the spectrum.

It has been determined that the magnitudes of the DC and AC components influence the accuracy of the saturation estimates and these magnitudes depend on the sensor design being used, the specifications of components used in the sensor, and how the sensor has been applied to the patient. The invention advantageously utilizes this knowledge to provide an oximeter system capable of providing indications of the accuracy and reliability of the saturation estimates. Additional features are provided by the invention based on the analysis of the measured DC and AC components, as described below.

Figure 4:
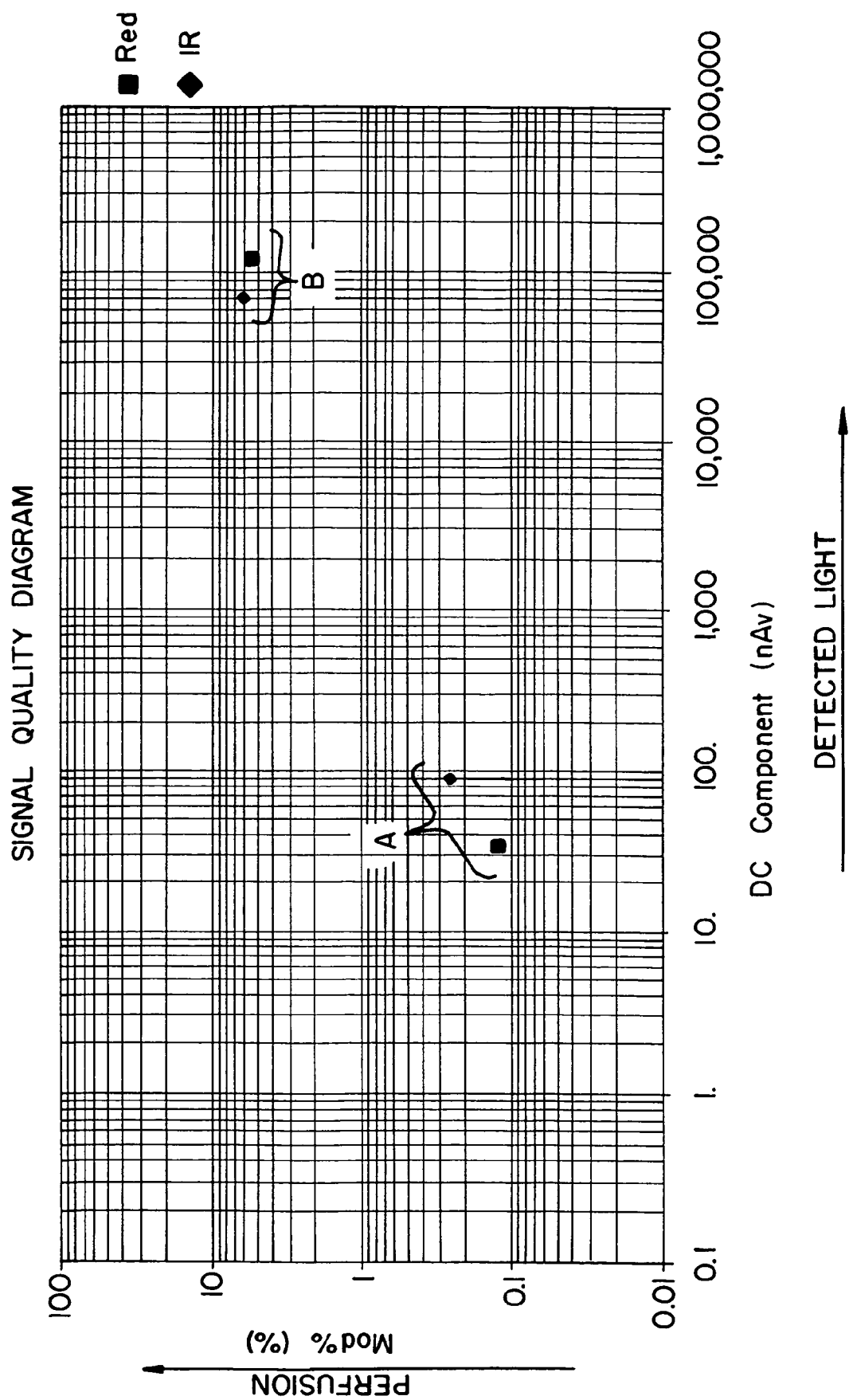
FIG. 4 shows a signal quality diagram that includes data of the measured DC and AC components.

FIG. 4 shows a signal quality diagram that includes data of the measured DC and AC components. The vertical axis of the signal quality diagram corresponds to the modulation percentage (Mod %) which is calculated as shown in equation (3) for each of the red and infrared signals. The horizontal axis corresponds to the DC component and is in units of virtual nano Amperes (nAv) and is given by equation (4). As shown in FIG. 4, both vertical and horizontal axes are plotted on a logarithmic scale.

As noted above, the detected optical waveform includes an AC component and a DC component. The DC component is plotted on the horizontal axis and the ratio of AC to DC is expressed as a percentage (e.g., Mod %) and plotted on the vertical axis. Since two different optical signals are measured (i.e., for the red and infrared wavelengths), two points are generated and plotted on the signal quality diagram to uniquely identify the AC and DC components of both the red and infrared optical signals. In FIG. 4, the data points corresponding to the red wavelength are identified by a square and the data points corresponding to the infrared wavelength are identified by a diamond.

FIG. 4 shows the relative positions of two data points associated with two patients on the signal quality diagram. For a (stable) patient and over a short duration (i.e., of few pulses), all four Ratrat constituents (Red AC, DC; and Infrared AC, DC) remain approximately constant. The data points for patient A indicate a patient with low light levels (i.e., low DC component values) and low modulation (i.e., low Mod %). These data points could correspond to data from, for example, a chubby, dark-skinned neonate who has poor perfusion, or a reflectance sensor applied to a poorly perfused site (i.e., on the foot). Conversely, the data points for patient B indicate a very translucent patient with good perfusion that results in high light levels and high modulation.

The pair of data points for each patient, one data point for red wavelength and one for infrared wavelength, defines the patient's current (Ratrat) conditions. Equivalently, the pair of data points describes the oximeter's "operating point," when the oximeter is monitoring that patient. For a particular patient, the pair of data points can be used to estimate the patient's saturation using equation (5) and a table for saturation versus Ratrat. For example, the Ratrat for patient A is approximately 0.12/0.25 or 0.48. For a typical oximeter, this Ratrat corresponds to a saturation of approximately 100%. The Ratrat for patient B is approximately 6/7 or 0.86, which corresponds to a saturation of approximately 85%.

In an embodiment, for each particular combination of oximeter model and sensor model, data points are collected for numerous "patients." These data points can be collected under a controlled test environment where true oxygen saturation is known, and an accuracy of the saturation estimated from the red and infrared signals can be determined. Based on the collected data, the diagram can be partitioned into regions corresponding to different levels of quality and accuracy in the saturation estimate. The regions also indicate a quality of the detected signals. Each region is defined by a signal boundary.

The signal boundaries are dependent on many factors such as the monitor type, sensor type, specifications of components in the sensor (e.g., wavelength, LED characteristics), and other factors. In an embodiment, sensor specific boundaries are stored in the sensor memory or other locations associated with the sensor.

Figure 5:
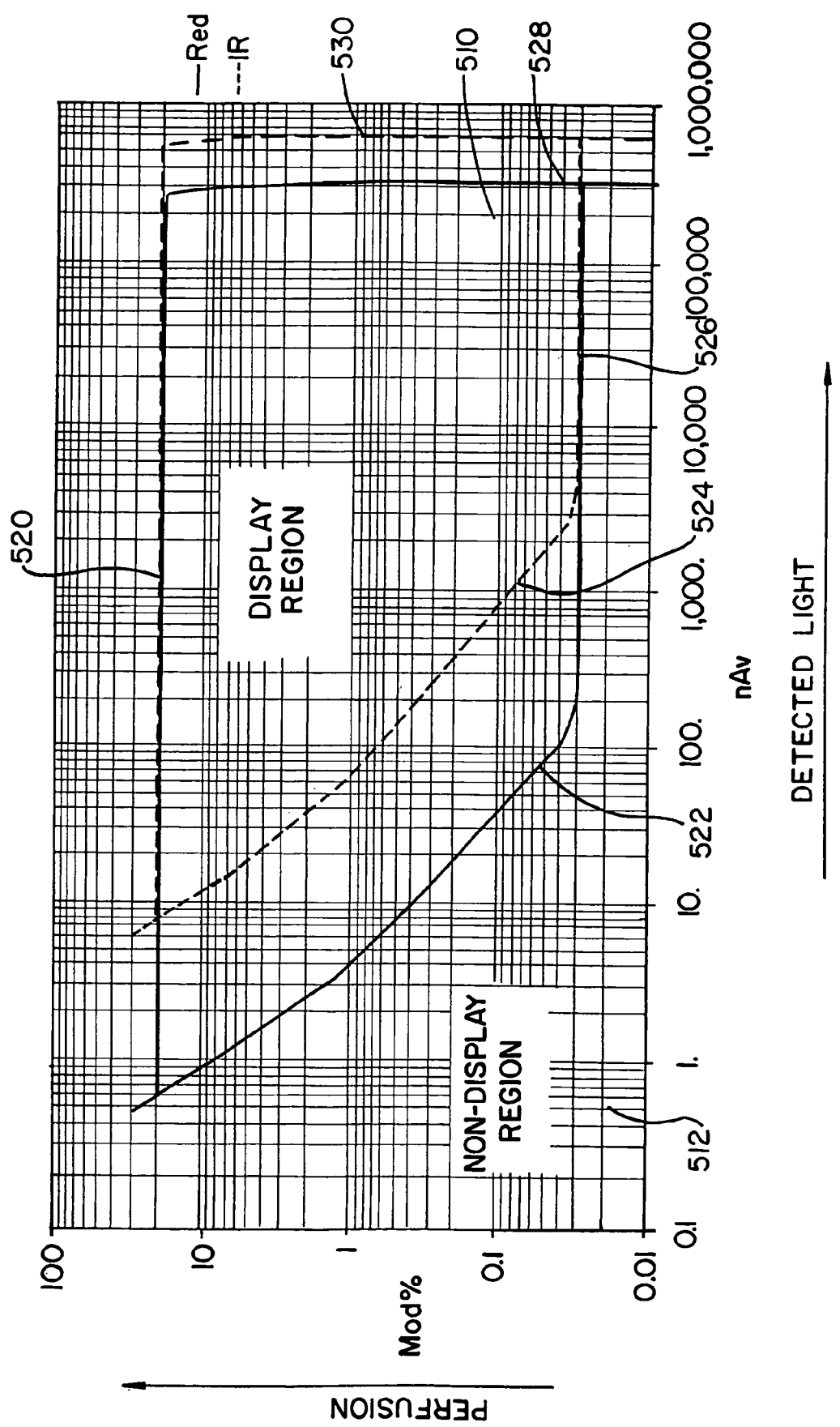
FIG. 5 shows a signal quality diagram having defined regions corresponding to different confidence levels in the saturation estimate.

FIG. 5 shows a sensor signal quality diagram having defined regions corresponding to different confidence levels in the saturation estimate. A display region 510 defines a portion of the signal quality diagram associated with saturation estimates that satisfy a predetermined quality and accuracy level and merit posting (or displaying) on the monitor. Display region 510 includes the set of "patient conditions" resulting in sufficiently accurate saturation estimates for a particular application. Accordingly, when the data points fall within display region 510, the saturation estimate (which is derived from the data points) is posted. Conversely, when the data points fall outside display region 510 into a non-display region 512, the saturation estimate corresponding to these data points is not posted on the oximeter display. Non-display region 512 lies outside, and generally surrounds, display region 510.

The DC signal corresponding to the red LED is generally "weaker" than the detected signal from the infrared LED. Since this characteristic is known a priori, the oximeter can be designed to account for this difference. In one implementation, the red LED is associated with a first display region and the infrared LED is associated with a second display region. For example, referring to FIG. 5, the red display region is defined by lines 520, 522, 526, and 528, and the infrared display region is defined by lines 520, 524, 526, and 530. Since the red signals are generally weaker than the infrared signal, the boundary of the red display region tends to be closer to the lower left corner of the signal quality diagram.

The display region may be dependent on numerous operating conditions. For example, ambient light typically adds to the detected optical signals (i.e., increases the DC components) and thus may alter the display region. In this case, the display region could be adjusted to account for the perturbation of the signal caused by the (or distortion introduced by) ambient light.

Figure 6:
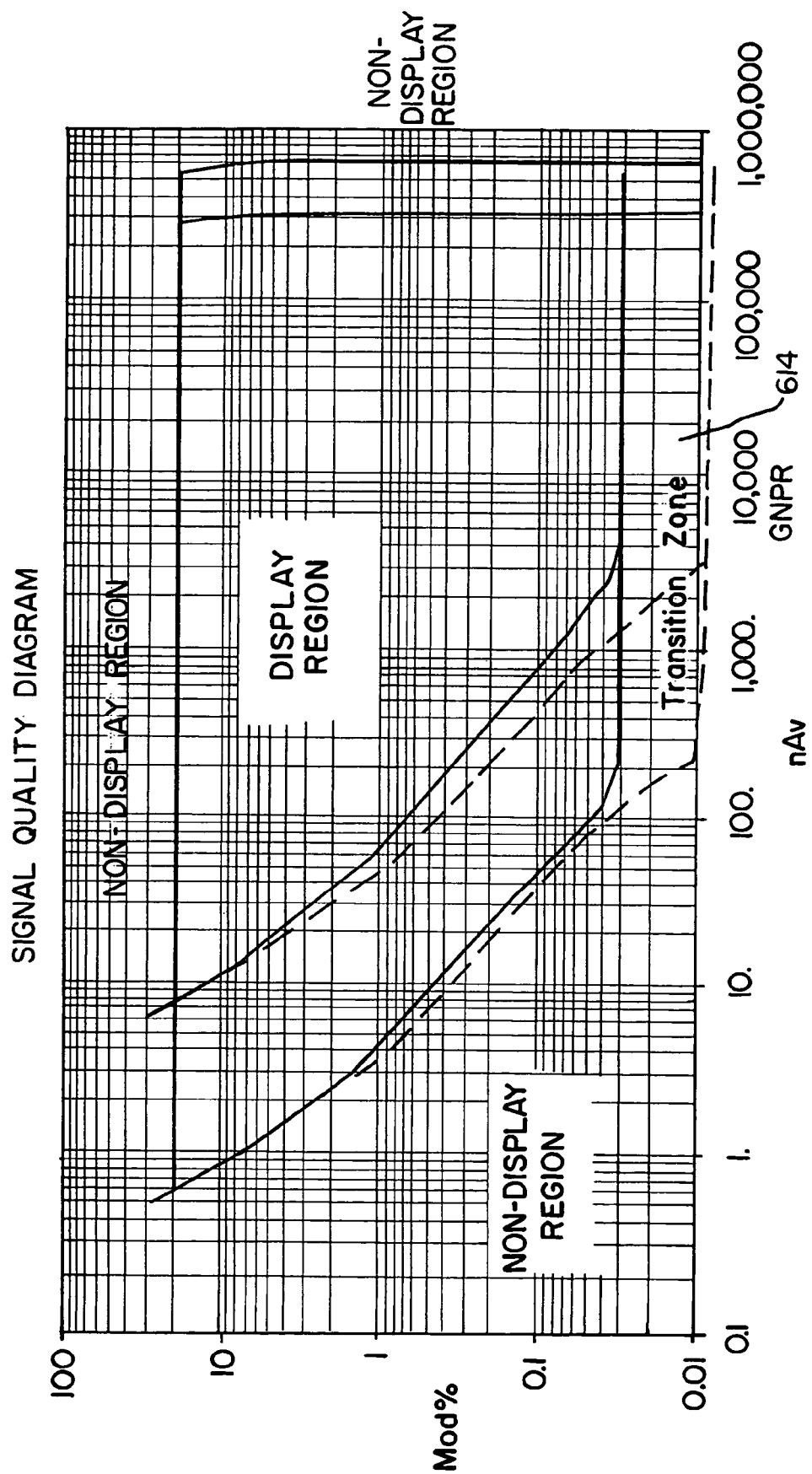
FIG. 6 shows a signal quality diagram having defined display and non-display regions (similar to those of FIG. 5) and transition zones.

FIG. 6 shows a signal quality diagram having defined display and non-display regions (similar to those of FIG. 5) and a transition zone 614. Transition zone 614 includes regions of the diagram that lie between the display and non-display regions. The transition zone represents regions associated with a different (e.g., intermediate) quality and accuracy level than those of the display and non-display regions. A different set of criteria can be used when evaluating data points that fall within the transition zone, as described below.

The regions shown in FIGS. 5 and 6 are only representatives of a particular oximeter/sensor combination and for a particular set of operating conditions. Each oximeter (or each oximeter model or type) is typically associated with its own set of display and non-display regions, which may differ from those shown in FIGS. 5 and 6. Some oximeters may even have poorly defined non-display regions, where the boundaries vary depending on a set of factors. These factors include the signal-to-noise ratio (SNR) of the oximeter, the amount of ambient light, the wavelength of the sensor LEDs, and so on.

In an embodiment, the oximeter operates in accordance with the following set of rules:

If both data points (i.e., for the red and infrared signals) fall within their respective display regions, the oximeter posts the result (e.g., the saturation estimate, and heart rate).

If either data point falls within its non-display region, the oximeter does not post the result.

In all other cases, the oximeter may or may not post the result. These cases include instances in which one of the signals falls in the transition zone and neither signal falls in the non-display region.

Thus, the saturation estimate is posted if the modulation percentage (Mod %) and the light level (DC components) for both the red and infrared wavelengths fall within the bounded areas of their respective display regions. In an embodiment, if the red signal falls within the red non-display region or if the infrared signal falls within the infrared non-display region, or both, then the oximeter does not post the saturation estimate. It can be noted that other sets of rules can also be applied. For example, in another embodiment, the result is posted if one of the data points falls within its display region and the other data point falls within the transition zone. In yet another embodiment, the oximeter posts the saturation estimate and also indicates either the regions in which the data points fall or a confidence level based on the regions in which the data points fall.

For clarity, FIG. 5 shows only display and non-display regions. These regions correspond to data points that are to be displayed and not displayed. However, additional regions can be defined within the signal quality diagram, with the additional regions corresponding to different confidence levels in the saturation estimate. Generally, the confidence level is high for data points that fall near the center of the diagram and decreases as the data points move away from the center. For the embodiment having multiple confidence levels, the oximeter can display the saturation estimate along with the confidence level.

For example, an "inactive" region can be defined and used to indicate when a sensor is not applied to a patient. The inactive region may be used to detect and notify when the sensor has been removed (i.e., fallen off) the patient. The inactive region lies outside the display and transition regions, correlates to measurements from sensors that are not attached to patients, and typically comprises a portion of the non-display region. This region can be defined through simulation or through empirical measurements. The oximeter computes the data points in the manner described above. If the data points fall inside the inactive region, the oximeter displays an indication that the sensor has been removed from the patient.

Figure 7:
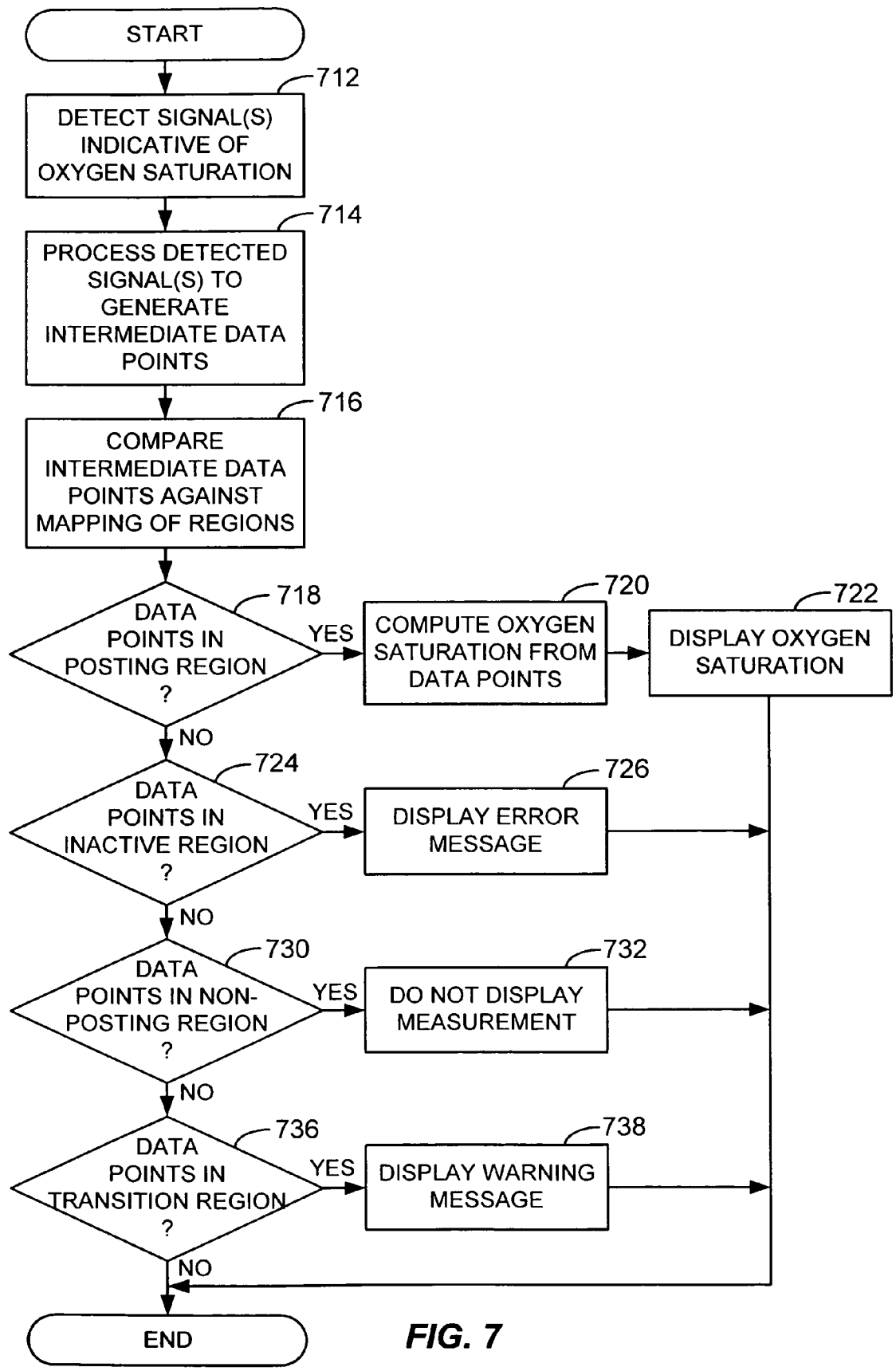
FIG. 7 shows a flow diagram of an embodiment of the measurement posting process of the invention.

FIG. 7 shows a flow diagram of an embodiment of the measurement display process of the invention. At a step 712, one or more signals indicative of a physiological parameter are detected. For an oximeter used to measure oxygen saturation, this detecting step may include, for example, receiving optical signals from two LEDs and conditioning these signals. At a step 714, the detected signal(s) are processed to generate intermediate data points. For oxygen saturation, this processing step may include filtering the data samples to generate DC and AC components, and using these components to generate the modulation percentage (Mod %). The intermediate data points would include filtered values for the DC component and computed values of the modulation percentage. The intermediate data points are then compared against a signal quality diagram (step 716). This diagram is generated previously, in a manner described above.

At step 718, it is determined whether the intermediate data points fall within the display region. If the answer is yes, the physiological parameter is estimated based on the detected and processed signal(s). For example, the oxygen saturation can be estimated from the computed Mod % for the two LEDs using equation (5). At step 722, the estimated physiological parameter is displayed, and the process terminates.

If it is determined at step 718 that the data points do not fall within the display region, a determination is made whether the data points fall within the inactive region (step 724). If the answer is yes, an error message is displayed at step 726. This error message may inform the clinician of the error data points (e.g., "ERROR MEASUREMENT"), provide a suggestion (e.g., "TRY ANOTHER SITE"), and so on. The process then terminates. In some embodiments of the invention, step 724 is not performed.

If it is determined at step 724 that the data points do not fall within the inactive region, a determination is made whether the data points fall within the non-display region, at a step 730. If the answer is yes, the measurement is not displayed. An error message may be displayed to inform the clinician. This error message may inform the clinician of the invalid data points (e.g., "INVALID MEASUREMENT" or "WEAK SIGNAL"), provide a suggestion (e.g., "TRY ANOTHER SITE"), and so on. The process then terminates.

If it is determined at step 730 that the data points do not fall within the non-display region, a determination is made whether the data points fall within the transition region, at step 736. If the answer is yes, a warning message may be displayed to warn the clinician. This warning message may indicate that the data points are of questionable accuracy (e.g., "INACCURATE MEASUREMENT" or "WEAK SIGNAL"), provide a suggestion (e.g., "TRY ANOTHER SITE"), and so on. The physiological parameter may also be computed and displayed along with the warning message. The process then terminates. In some embodiments of the invention, step 736 is not performed.

Figure 8:
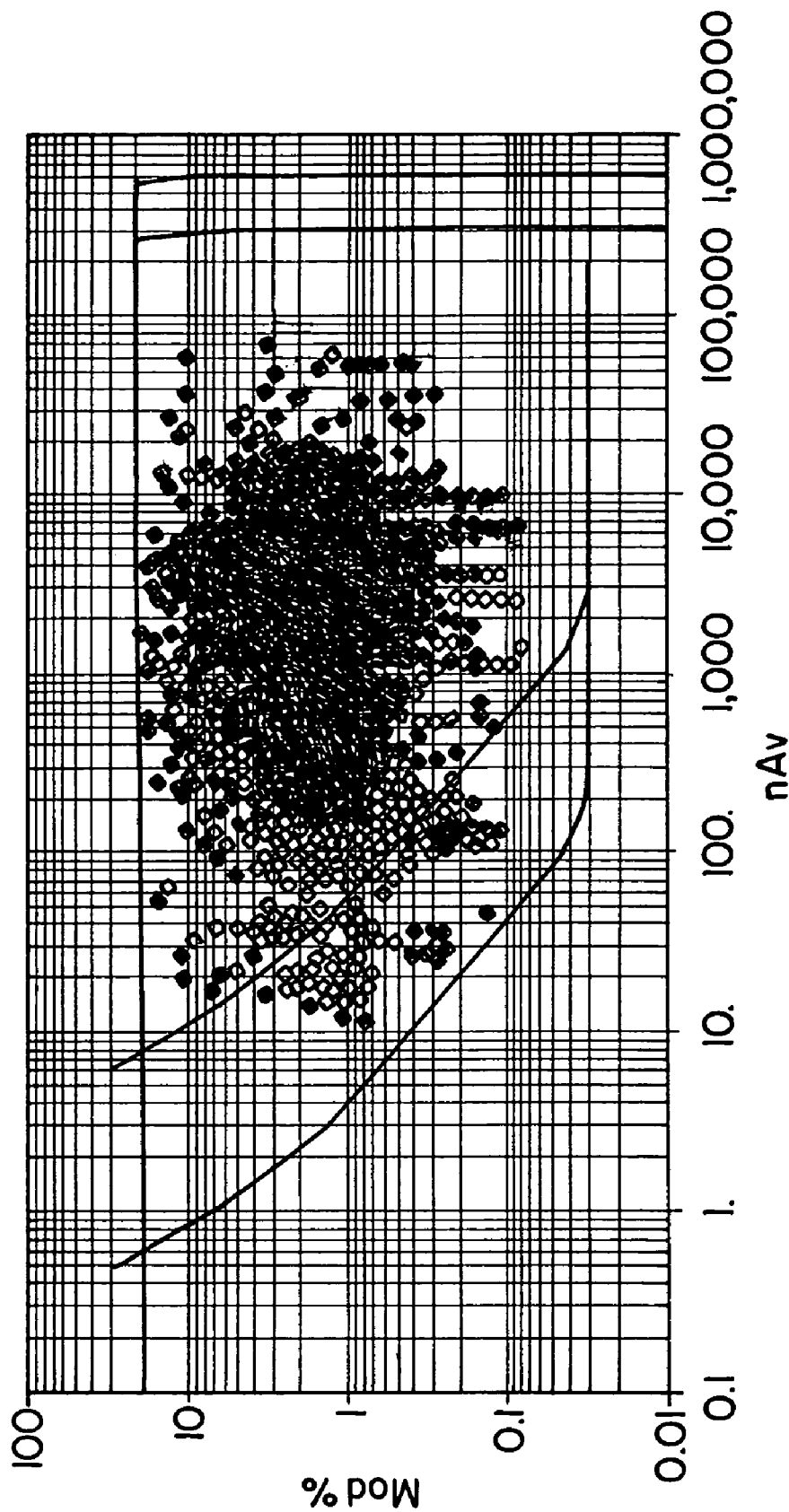
FIG. 8 shows a signal quality diagram with data collected from a patient population.

FIG. 8 shows a signal quality diagram with data collected from a patient population. The patient data can be used to define the display and non-display regions, to characterize the patient population's mean modulation percentage and mean nAv for both red and infrared wavelengths, to characterize measurement ambiguity that is indicative of the instrument's accuracy, or a combination of the above. Ambiguity as used herein, which is an approximate indication of instrument error, is the sum of the mean error (bias) of an instrument and the stability of the readings obtained (wander). The stability of the readings obtained (wander) is the standard deviation of the instrument readings.

The ambiguity, or estimated error, for various combinations of modulation and DC component are then plotted on the signal quality diagram. The average saturation, saturation bias, saturation wander, and ambiguity can be computed using equal weighting (i.e., giving the same importance for each data point) or unequal weighting that accounts for population statistics (i.e., giving less importance to data points that occur more rarely). Signal specification boundaries can also be obtained for a particular patient sub-population (e.g., perinatal patients) to further improve accuracy in the measurement reporting when the instrument is used for that particular patient sub-population.

Figure 9:
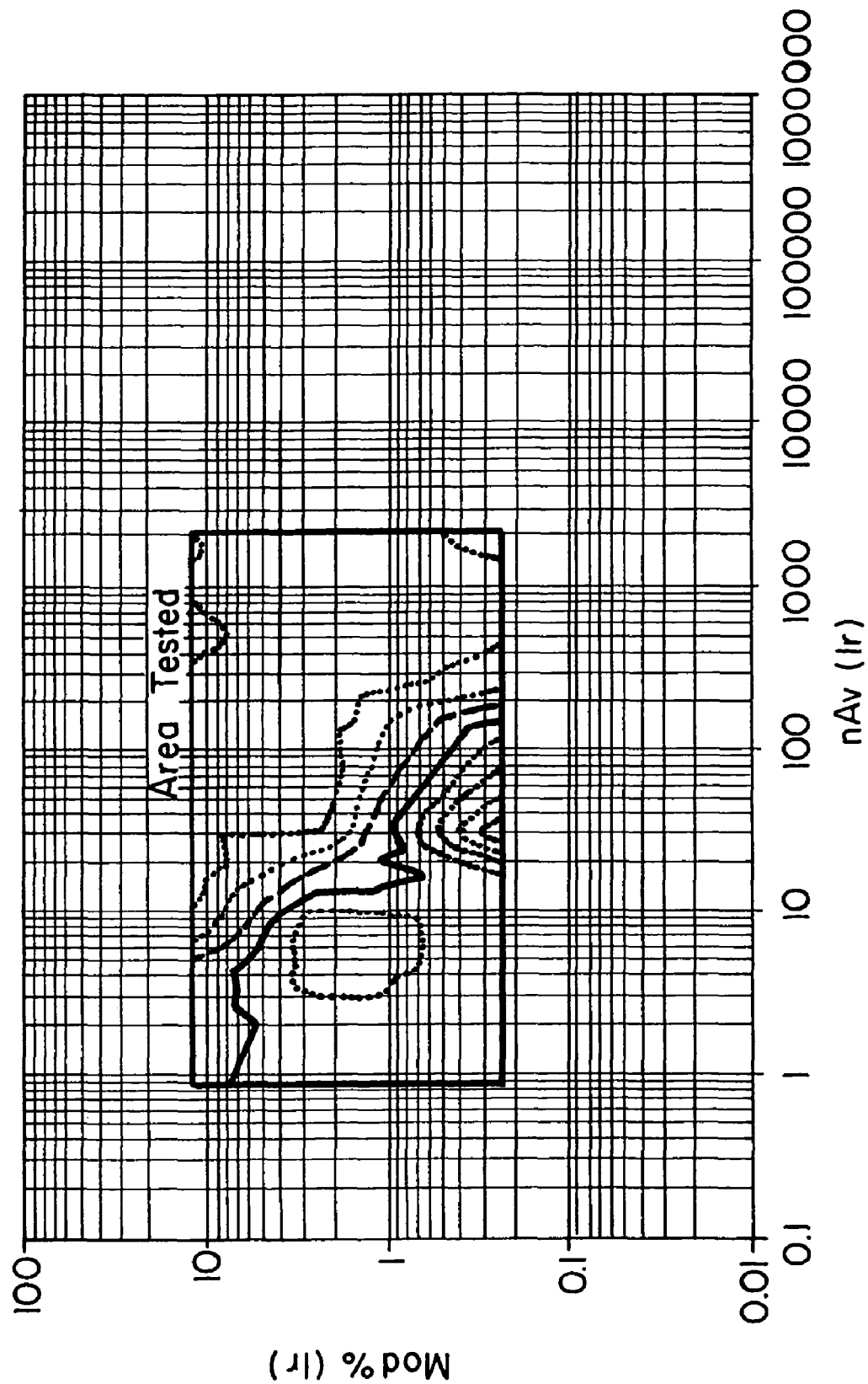
FIG. 9 shows a signal quality diagram that includes ambiguity contours plotted over a portion of the display region.

FIG. 9 shows a signal quality diagram that includes ambiguity contours plotted over a portion of the display region. Each contour line corresponds to a particular ambiguity, in saturation points. As an example, at an infrared operating point of 10 nAv and three percent modulation, the plots show an ambiguity of between 10 and 12 saturation points. The contour lines can be generated by collecting data points, grouping the data points that have similar infrared DC components, and selecting a representative ambiguity for those data points. The selected ambiguities for the groups of data points are plotted as a two-dimensional contour plot.

In an embodiment, the largest ambiguity in each group is selected as representative of the group and a contour plot of the worse case ambiguity is generated. This information is useful, for example, in an oximeter having a guaranteed limit on the saturation ambiguity, and only data points within the guaranteed limit are posted. Other variations of the contour plots shown in FIG. 9 are possible. For example, contour plots can be generated for: (1) the worst case ambiguity, (2) the average ambiguity, (3) the worst case or average absolute value of the bias, (4) the worst case or average value of the wander, and others. The average ambiguity contour plots are generated based on the average of the ambiguities obtained for each group, and are useful for indicating typical ambiguity that is likely to occur for that modulation and infrared DC component.

The contour plots on the signal quality diagram can also be adjusted for, or take into account, different pulse rates and abnormal heart rhythms such as arrhythmias, premature ventricular contractions, bigeminy, fibrillation, cardiac arrest, and other cardiac pathologies.

The invention provides advantages not available in conventional oximeters. For example, by detecting data points corresponding to saturation estimates having a low degree of confidence and discarding these estimates (or indicating the low degree of confidence), the invention provides an oximeter having improved diagnostic accuracy and reliability. This ensures that the results relied upon by the clinician meet a predetermined reliability criteria. The invention may also be used to detect and notify when the sensor has been removed (i.e., fallen off) the patient, as described above.

The oximeter of the invention can also be used to assist the clinician take more accurate measurements. This is a particularly useful application of the invention since it is known that some clinicians move the sensor to various parts of the patient in an attempt to obtain better readings. To assist the clinician, the oximeter can be programmed to display an indicator signal that indicates whether a selected site is good or poor for application of the sensor. This prompt may also be used to assist a less experienced clinician administer the saturation measurement.

The invention can be used for various physiological measurements. The application of the invention to pulse oximetry has been described as only one preferred embodiment. The invention can also be applied to other physiological measurements such as ECG, blood pressure, temperature, heart rate, and so on. Accordingly, the invention is not to be limited for use only with oximetry or pulse oximetry.

The foregoing description of the preferred embodiments is provided to enable any person skilled in the art to make or use the present invention. Various modifications to these embodiments will be readily apparent to those skilled in the art, and the generic principles defined herein may be applied to other embodiments without the use of further invention. For example, the invention can be applied to measurements of other physiological characteristics. Thus, the present invention is not intended to be limited to the embodiments shown herein but is to be accorded the widest scope consistent with the principles and novel features disclosed herein.

What is claimed is:

1. A system for detecting at least one physiological characteristic of a patient, comprising:
   a sensor, comprising:
      a detector adapted to generate signals indicative of the at least one physiological characteristic; and
      a memory storing data defining at least one sensor specific boundary that is indicative of a transition between a signal regime considered to be normal for the sensor in the sensor's usual application and a signal regime considered to be abnormal for the sensor in the sensor's usual application, wherein the at least one sensor specific boundary is indicative of a quality of the signals generated by the sensor and an accuracy of an estimated physiological condition of the patient; and
   a monitor, comprising:
      a first receiving circuit configured to receive the signals indicative of the at least one physiological characteristic from the sensor;
      a first processing circuit configured to provide the estimated physiological condition of the patient based on the signals;
      a second receiving circuit configured to receive the data defining the at least one sensor specific boundary for the signals from the sensor; and
      a second processing circuit configured to compare the signals against the sensor specific boundary and to generate an indication of the accuracy of the estimated physiological condition, wherein the second processing circuit is further configured to determine whether the signals are within the normal regime or the abnormal regime.

2. The system of claim 1, wherein the sensor specific boundary is characteristic of a model of the sensor or of individual components used in the sensor.

3. The system of claim 1, wherein the memory is physically located on one of a sensor body, sensor cable, sensor connecting plug, or a sensor adapter module.

4. The system of claim 1, wherein the signals are based on light emissions scattered from the patient, the light emissions having first and second wavelengths, the light emissions each having an AC modulation component.

5. The system of claim 1, wherein the detector is a photodetector.

6. The system of claim 1, wherein the signals are indicative of an arterial oxygen saturation of the patient.

7. The system of claim 1, wherein the memory is adapted to be written to only once to prevent erasure of the data during sensor operation.

8. A method of manufacturing a system, comprising:
   providing a sensor comprising a detector configured to generate signals that are indicative of a physiological characteristic of a patient;
   providing a memory coupled with the sensor, the memory storing data defining at least one sensor signal specification boundary for the signals, the at least one sensor signal specification boundary being indicative of a transition between a signal regime considered normal for the sensor in the sensor's usual application and a signal regime considered to be abnormal, wherein the at least one sensor signal specification boundary is indicative of a quality of the signals generated by the sensor and an accuracy of an estimated physiological condition of the patient, and providing a monitor configured to receive the signals indicative of the physiological characteristic from the sensor, to provide the estimated physiological condition of the patient based on the signals, to receive the data defining the at least one sensor signal specification boundary for the signals from the sensor, to compare the signals against the at least one sensor signal specification boundary, and to generate an indication of the accuracy of the estimated physiological condition and to determine whether the signals are within the normal regime or the abnormal regime based on the comparison of the signals to the at least one sensor signal specification boundary.

9. The method of claim 8, wherein the at least one sensor signal specification boundary is characteristic of a model of the sensor or of individual components used in making the sensor.

10. A method of manufacturing a system, comprising:

providing a sensor comprising a detector configured to generate signals that are indicative of a physiological characteristic of a patient;

providing a memory coupled to the sensor, the memory storing data defining at least one sensor signal specification boundary for the signals, the at least one sensor signal specification boundary being indicative of a transition between a signal regime considered normal for the sensor in the sensor's usual application and a signal regime considered to be abnormal, wherein the at least one signal specification boundary is characteristic of a model of the sensor or of individual components used in the sensor; and providing a monitor configured to receive the signals from the sensor, to receive the data defining the at least one sensor signal specification boundary for the signals from the sensor, to determine an estimated physiological condition of the patient based on the signals, to compare the received signals with the at least one sensor signal specification boundary, and to generate an indication of the accuracy of the estimated physiological condition and to determine whether the signals are within a normal regime for the sensor in the sensor's usual application or an abnormal regime for the sensor in the sensor's usual application based on the comparison of the received signals to at least one sensor signal specification boundary.

11. A method of operating a system for detecting at least one physiological characteristic, comprising:

generating, with a sensor, signals from a patient that are indicative of the physiological characteristic; and accessing a memory coupled to the sensor to facilitate transmission of data defining at least one sensor signal specification boundary, the sensor signal specification boundary being indicative of a transition between a signal regime considered normal for the sensor in the sensor's usual application and a signal regime considered to be abnormal, wherein the at least one sensor specific boundary is indicative of a quality of the signals generated by the sensor and an accuracy of an estimated physiological condition of the patient;

transmitting from the sensor to a monitor the signals indicative of at least one physiological characteristic;

determining the estimated physiological condition of the patient via the monitor based on the signals;

transmitting data defining the at least one sensor signal specification boundary for the signals from the sensor to the monitor;

comparing via the monitor the signals against the sensor signal specification boundary;

generating via the monitor an indication of the accuracy of the estimated physiological condition; and determining via the monitor whether the signals are within the normal regime or the abnormal regime.

12. The method of claim 11, wherein the sensor signal specification boundary is characteristic of a model of the sensor or of individual components used in the sensor.

13. A monitor for providing an indication of an accuracy of an estimated physiological condition of a patient, the monitor being coupleable to a sensor that generates signals indicative of at least one physiological characteristic of the patient, the monitor comprising:

a first receiving circuit configured to receive the signals indicative of the at least one physiological characteristic from the sensor;

a first processing circuit configured to provide an estimated physiological condition of the patient based on the signals;

a second receiving circuit configured to receive data defining at least one sensor signal specification boundary for the signals from the sensor, the sensor signal specification boundary being indicative of a quality of the signals generated by the sensor and an accuracy of the estimated physiological characteristic estimated from the signals, wherein the sensor signal specification boundary is indicative of a transition between a signal regime considered normal for the sensor in the sensor's usual application and a signal regime considered to be abnormal; and a second processing circuit configured to compare the signals against the sensor signal specification boundary and to generate an indication of the accuracy of the estimated physiological condition, wherein the second processing circuit is further configured to determine whether the signals are within the normal regime or the abnormal regime.

14. The monitor of claim 13, comprising a display device configured to display the estimated physiological characteristic.

15. The monitor of claim 13, wherein the normal regime is one in which the sensor is likely to be properly coupled to the patient and the abnormal regime is one in which the sensor is likely to have partially or fully decoupled from the patient.

16. The monitor of claim 13, wherein the second processing circuit is configured to compute an indication of whether the sensor is likely to be coupled to the patient or has partially or entirely decoupled from the patient.

17. The monitor of claim 13, wherein the monitor is a pulse oximetry monitor comprising:

a processor configured to determine whether the signals are within the normal regime; and a display configured to inform a user whether the signals are normal or abnormal.

18. The monitor of claim 13 wherein the monitor is a pulse oximetry monitor comprising:

a processor configured to determine whether the signals are within the normal regime or the abnormal regime; and an alarm that is triggered when the signals move from the normal regime to the abnormal regime.

19. A method of operating a monitor for providing an indication of an accuracy of an estimated physiological condition of a patient, comprising:

receiving from a sensor signals indicative of at least one physiological characteristic;

determining the estimated physiological condition of the patient based on the signals;

receiving data defining at least one sensor signal specification boundary for the signals, the sensor signal specification boundary being indicative of a quality of the signals detected by the sensor and an accuracy of the estimated physiological characteristic estimated from the signals, wherein the at least one sensor signal specification boundary is indicative of a transition between a signal regime considered normal for the sensor in the sensor's usual application and a signal regime considered to be abnormal;

comparing the signals against the sensor signal specification boundary;

generating an indication of the accuracy of the estimated physiological condition; and determining whether the signals are within the normal regime or the abnormal regime.

20. The method of claim 19, further comprising:
displaying the estimated physiological characteristic; and monitoring boundaries stored in the monitor.

21. A method of manufacturing a monitor for providing an indication of an accuracy of an estimated physiological condition of a patient, the monitor being coupleable to a sensor that generates signals indicative of at least one physiological characteristic of the patient, comprising:

providing a processing circuit configured to determine an estimated physiological condition of the patient based on the signals, compare the signals with at least one sensor signal specification boundary, generate an indication of the accuracy of the estimated physiological condition, and determine whether the signals are within a normal regime for the sensor in the sensor's usual application or an abnormal regime for the sensor in the sensor's usual application; and providing a receiving circuit configured to receive the signals from the sensor and receive data defining the sensor signal specification boundary for the signals from the sensor, the sensor signal specification boundary being indicative of a quality of the signals generated by the sensor and an accuracy of the estimated physiological characteristic, wherein the sensor signal specification boundary is indicative of a transition between the normal regime and the abnormal regime.

22. A system, for detecting at least one physiological characteristic of a patient, comprising:

a sensor, comprising:
a detector configured to generate signals that are indicative of the physiological characteristic;
a memory coupled to the sensor, the memory storing data defining at least one sensor signal specification boundary for the signals, the sensor signal specification boundary being indicative of a transition between a signal regime considered normal for the sensor in the sensor's usual application and a signal regime considered to be abnormal and being indicative of a quality of the signals generated by the sensor; and
an integrated circuit providing access to the memory to facilitate transmission of the data defining the at least one sensor signal specification boundary; and a monitor, comprising:
a processing circuit configured to determine an estimated physiological condition of the patient based on the signals, compare the signals with the at least one sensor signal specification boundary, generate an indication of the accuracy of the estimated physiological condition, and determine whether the signals are within the normal regime or the abnormal regime; and a receiving circuit configured to receive the signals indicative of the at least one physiological characteristic and to receive data defining the at least one sensor signal specification boundary, the sensor signal specification boundary being indicative of an accuracy of the estimated physiological characteristic.

23. A system for detecting at least one physiological characteristic of a patient, comprising:

a detector of a sensor adapted to generate signals indicative of the at least one physiological characteristic; and a memory coupled to or integral with the sensor storing data defining at least one specific boundary characteristic of a model of the sensor, the at least one specific boundary characteristic being indicative of a quality of the signals generated by the sensor and an accuracy of the estimated physiological characteristic estimated from the signals, wherein the at least one specific boundary characteristic is indicative of a transition between a normal signal regime considered to be of sufficient quality and accuracy for the sensor when applied to a patient and an abnormal signal regime considered to be of insufficient quality and accuracy for the sensor when applied to the patient, the memory adapted to allow transmission of the boundary to a monitor to enable the monitor to display the estimated physiological characteristic when the signals fall within the normal signal regime and to display an indication of when the signals fall within the abnormal signal regime; and the monitor, comprising:
a first receiving circuit configured to receive the signals indicative of the at least one physiological characteristic from the sensor;
a first processing circuit configured to provide the estimated physiological characteristic of the patient based on the signals;
a second receiving circuit configured to receive data defining at least one sensor signal specification boundary for the signals from the memory; and
a second processing circuit configured to compare the signals against the sensor signal specification boundary and to generate an indication of the accuracy of the estimated physiological characteristic, wherein the second processing circuit is further configured to determine whether the signals are within the normal regime or the abnormal regime.

24. The system of claim 23, wherein the normal signal regime is one in which the sensor is likely to be properly coupled to the patient and the abnormal signal regime is one in which the sensor is likely to have partially or fully decoupled from the patient.

25. The system of claim 23, wherein the at least one specific boundary is characteristic of individual components used in the sensor.

26. The system of claim 23, wherein the memory is physically located on one of a sensor body, sensor cable, sensor connecting plug, or a sensor adapter module.

27. The system of claim 23, wherein the signals are based on light scattered from the patient, the light having first and second wavelengths, and the first and second wavelengths each having an AC modulation component and a DC component.

28. The system of claim 23, wherein the detector is a photodetector.

29. The system of claim 23, wherein the signals are indicative of an arterial oxygen saturation.

30. The system of claim 23, wherein the memory is adapted to be written to only once to prevent erasure of the data during sensor operation.

31. A method of operating a system for detecting at least one physiological characteristic, comprising:
generating, with a sensor, signals from a patient that are indicative of the physiological characteristic;
accessing a memory coupled to the sensor to facilitate transmission of data defining at least one specific boundary characteristic of a model of the sensor, the at least one specific boundary characteristic being indicative of a quality of the signals generated by the sensor and an accuracy of the estimated physiological characteristic estimated from the signals, wherein the at least one specific boundary characteristic is indicative of a transition between a normal signal regime considered to be of sufficient quality and accuracy for the sensor when applied to a patient and an abnormal signal regime considered to be of insufficient quality and accuracy for the sensor when applied to the patient;
transmitting from the sensor to the monitor the signals indicative of at least one physiological characteristic;
determining the estimated physiological characteristic of the patient via the monitor based on the signals;
transmitting data defining the at least one specific boundary characteristic for the signals;
comparing via the monitor the signals against the at least one specific boundary characteristic;
generating via the monitor an indication of the accuracy of the estimated physiological characteristic; and
determining via the monitor whether the signals are within the normal signal regime or the abnormal signal regime.

32. The method of claim 31, wherein the normal signal regime is one in which the sensor is likely to be properly coupled to the patient and the abnormal signal regime is one in which the sensor is likely to have partially or fully decoupled from the patient.

33. A monitor for providing an indication of an accuracy of an estimated physiological condition of a patient, the monitor being coupleable to a sensor that generates signals indicative of at least one physiological characteristic of the patient, the monitor comprising:
a first receiving circuit configured to receive the signals indicative of the at least one physiological characteristic from the sensor;
a first processing circuit configured to provide an estimated physiological condition of the patient based on the signals;
a second receiving circuit configured to receive data defining at least one sensor signal specification boundary for the signals from the sensor, the sensor signal specification boundary being indicative of a quality of the signals generated by the sensor and an accuracy of the estimated physiological characteristic estimated from the signals, wherein the sensor signal specification boundary is indicative of a transition between a normal signal regime considered to be of sufficient quality and accuracy for the sensor when applied to a patient and an abnormal signal regime considered to be of insufficient quality and accuracy for the sensor when applied to the patient, and the at least one sensor signal specification boundary is characteristic of a model of the sensor or individual components of the sensor; and
a second processing circuit configured to compare the signals against the sensor signal specification boundary and to generate an indication of the accuracy of the estimated physiological condition, wherein the second processing circuit is further configured to determine whether the signals are within the normal regime or the abnormal regime.

34. The monitor of claim 33, comprising a display device configured to display the estimated physiological characteristic.

35. The monitor of claim 33, wherein the normal signal regime is one in which the sensor is likely be properly coupled to the patient and the abnormal signal regime is one in which the sensor is likely to have partially or fully decoupled from the patient.

36. The monitor of claim 33, wherein the second processing circuit is configured to compute an indication of whether the sensor is likely to be coupled to the patient or has partially or entirely decoupled from the patient.

37. The monitor of claim 33, wherein the monitor is a pulse oximetry monitor comprising:
a processor configured to determine whether the signals are within the normal signal regime; and
a display configured to inform a user whether the signals are normal or abnormal.

38. The monitor of claim 33, wherein the monitor is a pulse oximetry monitor comprising:
a processor configured to determine whether the signals are within the normal signal regime or the abnormal signal regime; and
an alarm that is triggered when the signals move from the normal signal regime to the abnormal regime.

39. A method of operating a monitor for providing an indication of an accuracy of an estimated physiological condition of a patient, comprising:
receiving from a sensor signals indicative of at least one physiological characteristic;
determining the estimated physiological condition of the patient based on the signals;
receiving data defining at least one sensor signal specification boundary for the signals, the sensor signal specification boundary being indicative of a quality of the signals detected by the sensor and an accuracy of the estimated physiological characteristic estimated from the signals, wherein the at least one sensor signal specification boundary is indicative of a transition between a normal signal regime considered to be of sufficient quality and accuracy for the sensor when applied to a patient and an abnormal signal regime considered to be of insufficient quality and accuracy for the sensor when applied to the patient, and the at least one sensor signal specification boundary is characteristic of a model of the sensor or individual components of the sensor;
comparing the signals against the sensor signal specification boundary;
generating an indication of the accuracy of the estimated physiological condition; and
determining whether the signals are within the normal signal regime or the abnormal signal regime.

40. The method claim 39, further comprising:
displaying the estimated physiological characteristic; and
monitoring boundaries stored in the monitor.

41. The method of claim 39, further comprising:
triggering an alarm when the signals move from the normal signal regime to the abnormal signal regime.

* * * * *